United States Patent
Beauchamp et al.

(10) Patent No.: US 9,957,307 B2
(45) Date of Patent: May 1, 2018

(54) EXPRESSION VECTORS FOR CELL-SURFACE EXPRESSION OF POLYPEPTIDES COMPRISING A TRANSMEMBRANE DOMAIN OF GLYCOPHORIN A

(71) Applicant: F. Hoffmann-La Roche AG, Basel (CH)

(72) Inventors: Jeremy Beauchamp, Riehen (CH); Anita Dreyer, Basel (CH); Hugues Matile, Basel (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 473 days.

(21) Appl. No.: 14/448,881

(22) Filed: Jul. 31, 2014

(65) Prior Publication Data
US 2014/0335097 A1  Nov. 13, 2014

Related U.S. Application Data

(63) Continuation of application No. 13/582,366, filed as application No. PCT/EP2011/052873 on Feb. 28, 2011, now abandoned.

(30) Foreign Application Priority Data

Mar. 2, 2010  (EP) .................................... 10155115

(51) Int. Cl.
*C07K 14/445* (2006.01)
*C12N 15/85* (2006.01)
*C07K 16/20* (2006.01)
*G01N 33/569* (2006.01)

(52) U.S. Cl.
CPC .......... *C07K 14/445* (2013.01); *C07K 16/205* (2013.01); *C12N 15/85* (2013.01); *G01N 33/56905* (2013.01); *C07K 2317/14* (2013.01); *C07K 2319/02* (2013.01); *C07K 2319/03* (2013.01); *C07K 2319/036* (2013.01); *C07K 2319/21* (2013.01); *C07K 2319/40* (2013.01); *C07K 2319/43* (2013.01); *C12N 2810/855* (2013.01)

(58) Field of Classification Search
None
See application file for complete search history.

(56) References Cited

FOREIGN PATENT DOCUMENTS

| | | |
|---|---|---|
| JP | 2003 235577 | 8/2003 |
| WO | 01/12845 A1 | 2/2001 |

OTHER PUBLICATIONS

Lemmon et al., J Biol Chem. Apr. 15, 1992;267(11):7683-9.*
Singer et al., Mol Biol Cell. Apr. 1998;9(4):901-15.*
Matsui et al., Gene. Apr. 30, 1989;77(2):325-32.*
Gu et al., Biochem Biophys Res Commun. May 31, 1991; 177(1 ):202-8.*
Einhauer et al., J Biochem Biophys Methods. Oct. 30, 2001;49(1-3):455-65.*
Borsig et al., Biochem Biophys Res Commun. Nov. 26, 1997;240(3):586-9.*
Xiao et al., Br J Pharmacol. May 1998;124(1 ):213-21.*
Invitrogen user manual for pcDNA3.1 (+) and pcDNA3.1 (–), version K printed Nov. 10, 2010.*
Pham et al., Mol Biotechnol. Oct. 2006;34(2):225-37.*
Abstract; Database WPI Week 200377, Thomson Scientific, London, GB AN 2003-820456 (Aug. 26, 2003).
Borsig et al., "Expression and Purification of His-Tagged β-1,4-Galactosyltransferase in Yeast and in COS Cells" Biochemical and Biophysical Research Communications 240:586-589 (1997).
Einhauer et al., "The FLAG™ peptide, a versatile fusion tag for the purification of recombinant proteins" J. Biochem. Biophys. Methods 49:455-465 ( 2001).
Glycophorin—Wikipedia, the free encyclopedia Retrieved from the internet on Aug. 29, 2012: http://en.wikipedia.org/wiki/Glycophorin (Jun. 24, 2011).
Gu et al., "Full length mouse glycophorin gene constructed using recombinant polymerase chain reaction" Biochemical and Biophysical Research Communications 177(1):202-208 ( 1991).
International Search Report issued in International Application No. PCT/EP2011/052873, dated Jul. 13, 2011, in 5 pages.
invitrogen™, User Manual for pcDNA™3.1(+) and pcDNA™3.1(–), Catalog Nos. V790-20 and V795-20, Verson K, printed Nov. 10, 2010, in 23 pages.
Lemmon et al., "Glycophorin A Dimerization Is Driven by Specific Interactions between Transmembrane α-Helices" The Journal of Biological Chemistry 267(11):7683-7689 ( 1992).
Matsui et al., "Isolation of the cDNA clone for mouse glycophorin, erythroid-specific membrane protein" Gene 77:325-332 ( 1989).
Puttikhunt, C. et al., "Production of anti-dengue NS1 monoclonal antibodies by DNA immunization", Journal of Virological Methods 109(1):55-61 (Apr. 2003).
Singer et al., "Dimerization of the Polymeric Immunoglobulin Receptor Controls Its Transcytotic Trafficking" Molecular Biology of the Cell 9:901-915 ( 1998).
Xiao et al., "Molecular cloning, expression and characterization of cDNA encoding a mouse $\alpha_{1a}$-adrenoceptor", British Journal of Pharmacology 124:213-221 (1998).

* cited by examiner

*Primary Examiner* — Michael Szperka

(57) ABSTRACT

The present invention provides expression vectors for cell-surface expression of polypeptides comprising a transmembrane domain of glycophorin A.

8 Claims, 5 Drawing Sheets

EXPRESSION VECTORS FOR CELL-SURFACE EXPRESSION OF POLYPEPTIDES COMPRISING A TRANSMEMBRANE DOMAIN OF GLYCOPHORIN A

CROSS REFERENCE TO RELATED APPLICATIONS

This application is a continuation of U.S. patent application Ser. No. 13/582,366, filed on Aug. 31, 2012, which is a national phase application of International Patent Application No. PCT/EP2011/052873, filed on Feb. 28, 2011, which claims priority to European Patent Application No. 10155115.8, filed on Mar. 2, 2010, the entire contents of which are incorporated herein by reference.

SEQUENCE LISTING

The instant application contains a Sequence Listing submitted via EFS-Web and hereby incorporated by reference in its entirety. Said ASCII copy, created on Jul. 31, 2014, is named P4953C1SeqList.txt, and is 73,505 bytes in size.

Since the discovery of monoclonal antibodies (mAbs) in 1975 by Kohler and Milstein, they have become molecular tools of inestimable value. Due to their high specificity, monoclonal antibodies (mAbs) are used for standard techniques throughout biology, being the key to the characterisation of protein function and distribution. Besides their usage in basic research, mAbs are also widely utilised as diagnostic and therapeutic agents. Due to this wide range of applications the generation of mAbs became a standard procedure. However, it can still be problematic, since for studies in physiological settings, it is important that the mAbs recognise the antigen in its native conformation.

Most commonly mAbs are raised against synthetic peptides derived from the predicted sequence of the target protein. Unfortunately, these Abs, though strongly reactive with peptide, frequently fail to recognise the native protein. Another standard procedure to generate mAbs uses recombinantly expressed protein. Prokaryotic expression systems are the most widely used expression hosts. But when studying mammalian surface proteins it is often necessary to use mammalian expression systems, as they are more likely to produce functional proteins with the appropriate disulfide-bonds, posttranslational glycosylations or proteolytic modifications. Purification of recombinant proteins is often a tedious undertaking, frequently representing a limiting step towards obtaining antibodies. Although introduction of affinity tags simplify purification, it often remains difficult to obtain recombinant protein in native conformation and in sufficient yield and purity. This applies most notably to membrane-associated proteins, as they are likely to lose their native structure during purification processes.

When attempting to generate mAbs capable of recognising the protein in its native context it is also critical to use protein in native conformation not only in the immunisation step but also for the screening procedure. Many standard hybridoma-screening protocols, such as the immobilisation of recombinant proteins on solid supports, may significantly alter protein conformation. For these reasons, mAbs selected on the basis of binding to a recombinant protein may not bind the same protein when it is in its native context.

Therefore, there is a need for an antigen expression system allowing the expression of antigens in native confirmation on the cell surface of cells.

In a first object the present invention provides a nucleic acid expression vector for cell-surface expression of proteins comprising in order a polynucleotide sequence encoding a secretion signal peptide, a cloning site for inserting a polynucleotide sequence encoding a protein to be expressed and a polynucleotide sequence encoding a transmembrane domain of glycophorin.

In a preferred embodiment of the nucleic acid expression vector, the transmembrane domain of glycophorin is the transmembrane domain of glycophorin A.

In a further preferred embodiment of the nucleic acid expression vector, the transmembrane domain of glycophorin A is the mouse glycophorin A transmembrane domain or the Armenian hamster glycophorin A domain.

In a further preferred embodiment of the nucleic acid expression vector, the mouse glycophorin A transmembrane domain comprises the amino acid sequence disclosed in Seq. Id. No. 1 and the Armenian hamster glycophorin A domain comprises the amino acid sequence disclosed in Seq. Id. No. 12.

In a further preferred embodiment of the nucleic acid expression vector, the secretion signal peptide is the secretion signal peptide of bee-venom melittin.

In a further preferred embodiment of the nucleic acid expression vector, the secretion signal peptide of bee-venom melittin comprises the amino acid sequence disclosed in Seq. Id. No. 2.

In a further preferred embodiment, the nucleic acid expression vector further comprises downstream (3') of the cloning site for inserting a polynucleotide sequence encoding a protein to be expressed a polynucleotide sequence encoding a FLAG tag comprising the amino acid sequence of Seq. Id. No. 3.

In a further preferred embodiment, the nucleic acid expression vector further comprises downstream (3') of the polynucleotide sequence encoding the transmembrane domain of glycophorin a polynucleotide sequence encoding a His tag, preferably a His tag comprising the amino acid sequence disclosed in Seq. Id. No. 4.

In a further preferred embodiment of the nucleic acid expression vector, the cloning site comprises the restriction enzyme cleavage sites of NheI, KpnI, BamHI, EcoRI, EcoRV and NotI.

In a further preferred embodiment, the nucleic acid expression vector comprises a polynucleotide sequence selected from the group consisting of Seq. Id. No. 5, Seq. Id. No. 13, Seq. Id. No. 14 and Seq. Id. No. 15.

In a further preferred embodiment of the nucleic acid expression vector, the protein to be expressed is a membrane associated protein.

In a second object, the present invention provides a cell comprising the vector of the present invention, preferably a mammalian cell, more preferably a HEK cell.

In a third object, the present invention provides a method for the generation of monoclonal antibodies against a specific protein comprising the steps:

a) immunisation of a non-human animal with cells expressing on its cell surfaces the specific protein using the vector of the present invention, b) isolating spleen cells of the non-human animals of step a), c) fusing the spleen cells of step b) with myeloma cells to generate B cell hybridomas and d) identification of B cell hybridomas expressing antibodies directed against the specific protein.

In a preferred embodiment of the method of the present invention, the non-human animal is a mouse or Armenian hamster.

"Nucleic acid expression vector" refers to an assembly which is capable of directing the expression of a sequence or gene of interest. The nucleic acid expression vector includes a promoter which is operably linked to the sequences or gene(s) of interest. Other control elements may be present as well. In addition, the vector may also include a bacterial origin of replication, one or more selectable markers, a signal which allows the vector to exist as single-stranded DNA (e.g., a M 13 origin of replication), a multiple cloning site, and a "mammalian" origin of replication (e.g., a SV40 or adenovirus origin of replication). A "vector" is capable of transferring gene sequences to target cells (e.g., viral vectors, non-viral vectors, particulate carriers, and liposomes). The vector is used to transport the foreign or heterologous DNA into a suitable host cell. Once in the host cell, the vector can replicate independently of the host chromosomal DNA, and several copies of the vector and its inserted (foreign) DNA may be generated.

The term "protein" as used herein, refers to a polymer of amino acids, and not to a specific length. Thus, peptides, oligopeptides and protein fragments are included within the definition of polypeptide.

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein (1975) Nature 256:495, or may be made by recombinant DNA methods (see, e.g. U.S. Pat. No. 4,816, 567 (Cabilly et al.) and Mage and Lamoyi (1987) in *Monoclonal Antibody Production Techniques and Applications*, pp. 79-97, Marcel Dekker, Inc., New York). The monoclonal antibodies may also be isolated from phage libraries generated using the techniques described in McCafferty et al. (1990) Nature 348:552-554, for example.

SHORT DESCRIPTION OF FIGURES

FIG. 1A shows the primary structure of human ABCA1 (Seq. Id. No. 7), rat TMEM27 (Seq. Id. No. 9) and *P. falciparum* PFF0620c (Seq. Id. No. 11) proteins used in the examples.

The domains used for the constructs described are marked with the diagonal lines with the amino acids at the N and C termini indicated;

Figure 3A:
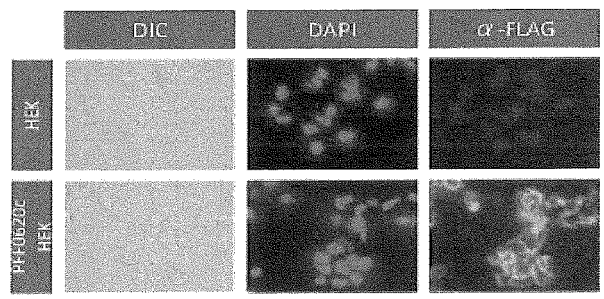
Figure 3B:
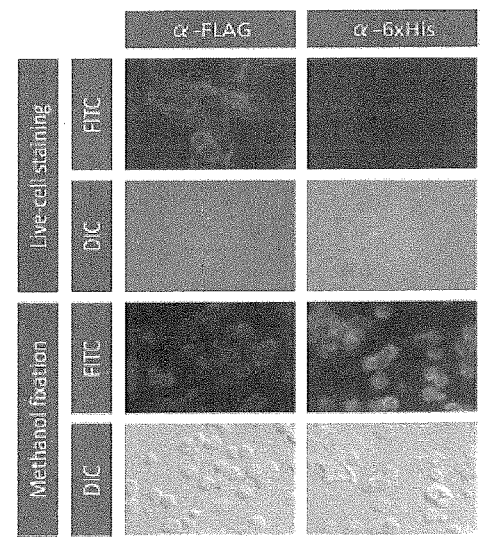
Figure 4:
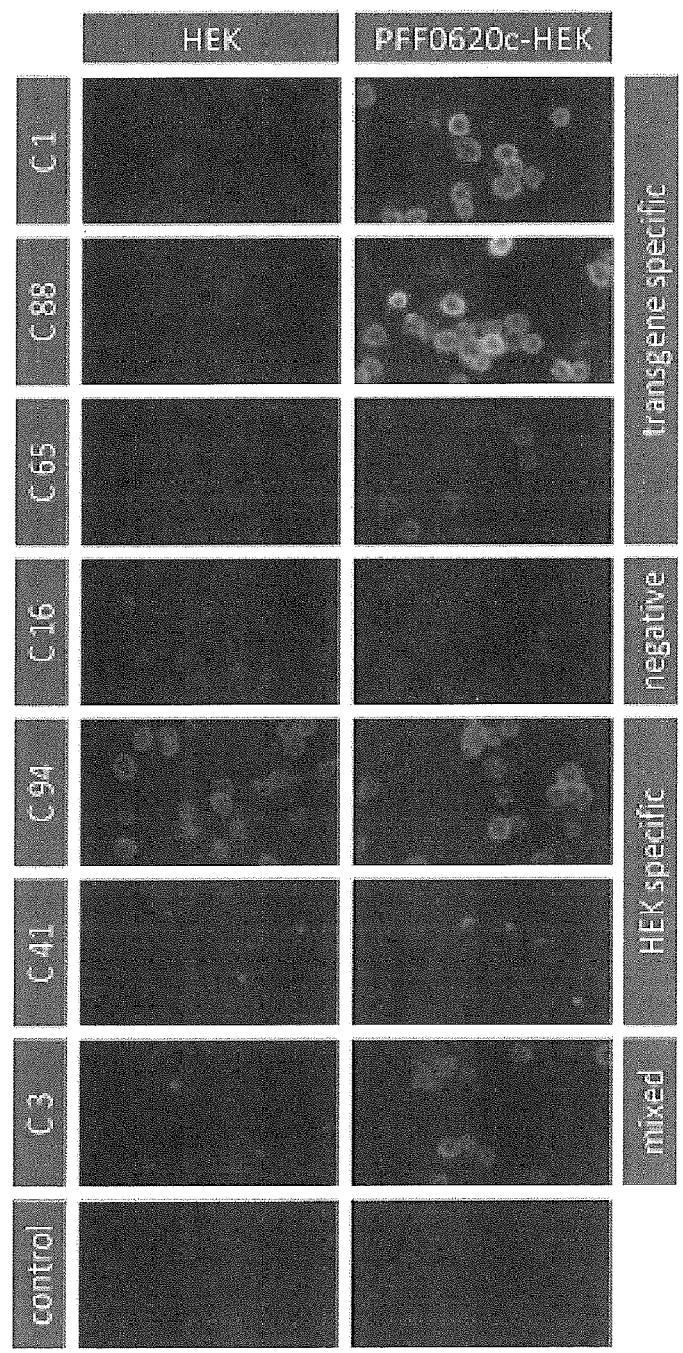
Figure 5:
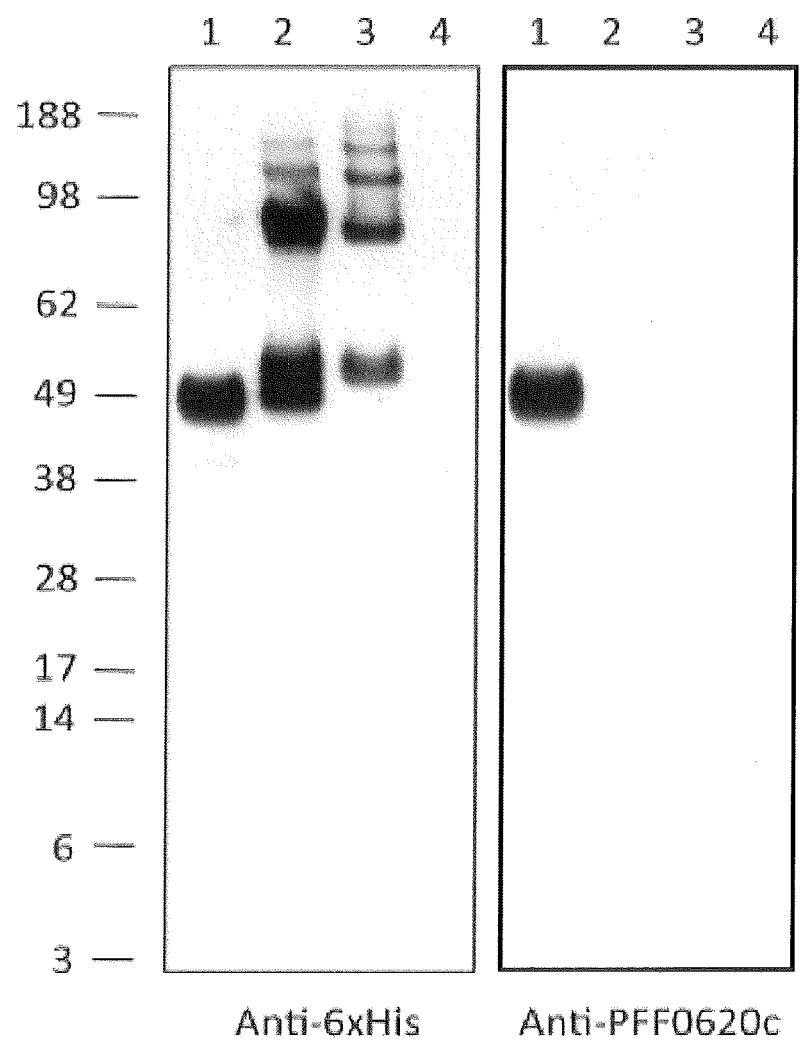

FIG. 3A shows cell-surface expression of PFF0620C on stably transfected HEK cells. Fluorescence (column 2 & 3) and differential interference contrast micrographs (column 1) of non-transfected HEK cells (line 1) and HEK cells displaying PFF0620C (line 2). Cells were grown on chamber-slides and stained without fixation with anti-FLAG antibody and FITC-labelled anti-mouse IgG antibodies. Nuclei were stained with DAPI;

FIG. 3B shows extracellular localisation of PFF0620C on stably transfected HEK cells. Fluorescence (line 1 & 3) and differential interference contrast micrograph (line 2 & 4) of PFF0620C-HEK cells after staining with anti-FLAG (left column) or anti-6×His antibodies (right column) and FITC-labelled anti-mouse IgG antibodies. With the anti-FLAG antibody living cells and methanol-fixed cells were stained, whereas the anti-His antibody only stained methanol-fixed cells, indicating intracellular localisation of the His-tag and extracellular localisation of the FLAG-tag together with the *P. falciparum* derived protein domain;

FIG. 4 shows the results of a screening of antibodies for binding to transfected cells. In a second step, all wells positive for IgG production were screened for antibody binding to transfected cells by IFA (immuno fluorescence assay). Transfected and non-transfected HEK cells spotted onto multiwell glass-slides were stained with individual hybridoma supernatants and analysed by fluorescence microscopy;

FIG. 5 shows a western blot analysis of the reactivity of generated monoclonal antibodies with the recombinant *P. falciparum* proteins. Specificity of representative monoclonal antibodies for the corresponding recombinant proteins is demonstrated by Western-blot analysis. Lysates of PFF0620c- (line 1), control pANITA2 constructs containing unrelated proteins (lines 2 & 3) and non-transfected HEK cells (line 4) were probed with anti-6×His mAb and an anti PFF0620cmAb generated as described, respectively.

Figure 6:
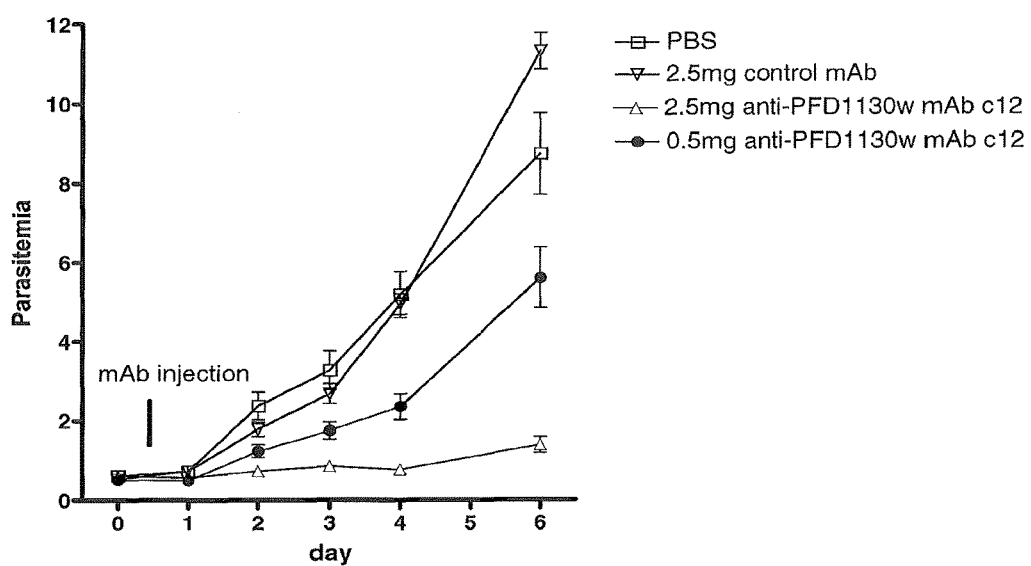

FIG. 6 shows that PFD1130w-specific monoclonal antibodies inhibit parasite growth in vivo.

EXAMPLES

Expression Proteins on the Cell Surface of Mammalian Cells.

Figure 1A:
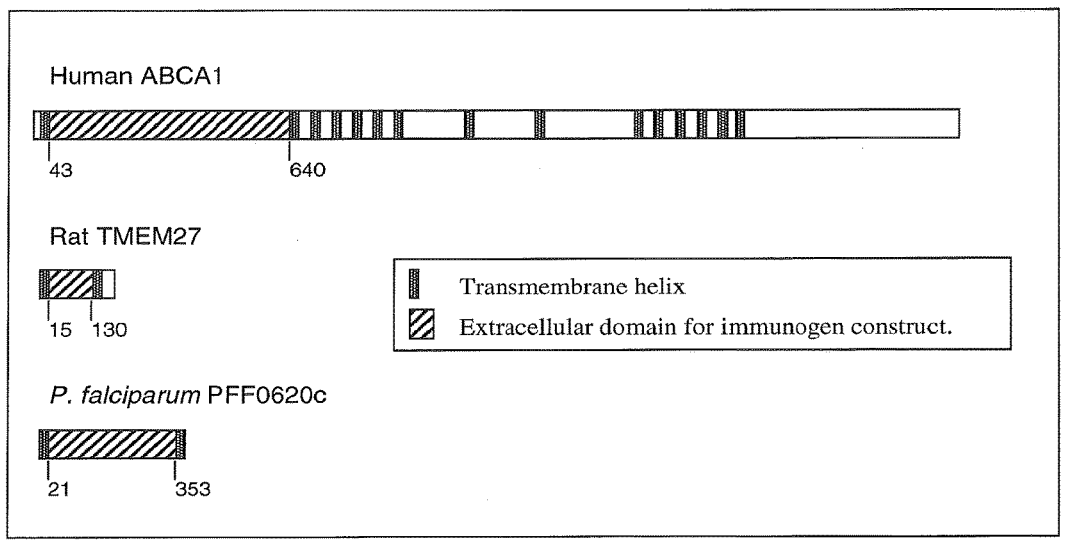
FIG. 1B shows schematic diagrams of the expressed protein constructs derived from the vectors described in the examples. The extracellular domains are equivalent to the ones shown in FIG. 1A.
Figure 1B:
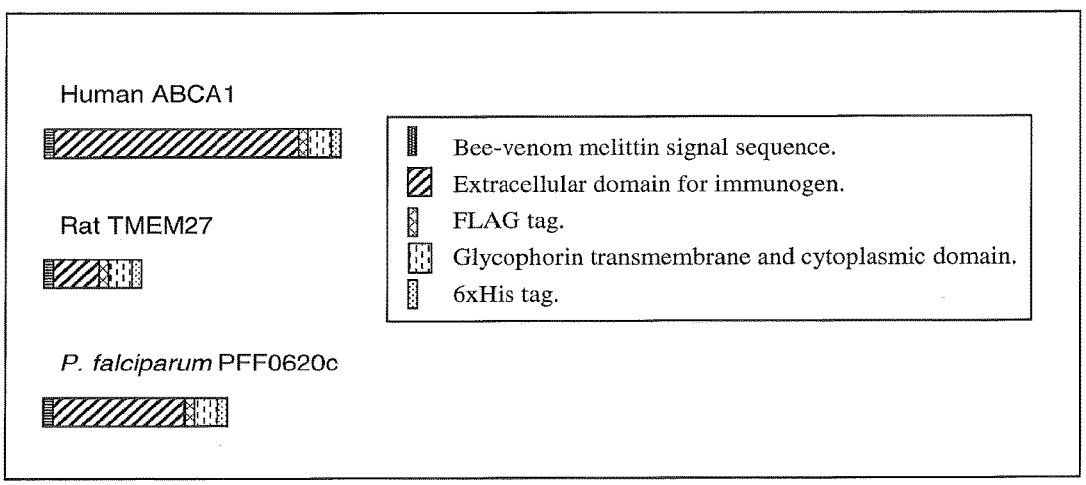

The *P. falciparum* ORF PFF0620c, human ABCA1 extracellular domain and rat TMEM27 extracellular domain were expressed on the cell surface of HEK cells using the expression plasmids pANITA2-PFF0620C; pANITA2-ABCA1 or pANITA2-TMEM27 respectively. To ensure high levels of expression on the cell surface, the genes were modified in several ways (FIG. 1): i. the endogenous sequences were codon-optimised for expression in mammalian cells and only predicted extracelluar domains were used; ii. the endogenous secretion signal sequences were replaced by the secretion signal sequence of bee-venom melittin; iii. for membrane anchoring the transmembrane domain encoding sequence of mouse glycophorin A was used instead of the predicted GPI-attachment signal sequence or predicted transmembrane domains; iv. to allow expression analysis, a FLAG tag was inserted N-terminally of the transmembrane domain and a 6×His tag was placed at the C-terminus. The two tags were positioned just before and after the transmembrane domain to facilitate verification of the extracellular localisation of the recombinantly expressed antigens.

HEK-derived cell lines expressing *P. falciparum* PFF0620c, human ABCA1 extracellular domain and rat TMEM27 extracellular domain were established by stable transfection.

To obtain highly expressing cell lines, transfectants were separated into high-expressing cell-pools by fluorescent-activated-cell-sorting after surface staining with anti-FLAG antibodies. The mean fluorescence intensity of the cells gated for sorting into the high-expressing cell pool was 2.1-4.3 times higher than that of all transfectants.

Figure 2:
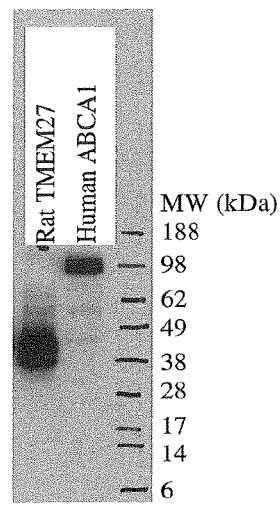
FIG. 2 shows a Western blot using anti-FLAG M2-HRP conjugated antibody (Sigma) of total cell lysates from HEK293 cells transfected with pANITA2-ABCA1 and pANITA2-TMEM27. Strong expression with bands at appropriate molecular weights is seen.

Human ABCA1 and rat TMEM27-expressing cell lines were tested for expression by Western blot analysis, showing a high level of expression of a protein with the expected molecular weight. (FIG. 2) Cell surface expression of the *P. falciparum* PFF0620c protein was shown by immunofluoresence analysis with anti-FLAG antibody yielding strong signals on living cells. (FIG. 3) In contrast, staining with anti-6xHis antibody gave strong signals only on methanol fixed cells but not on living cells (FIG. 3B). These results verified that PFF0620c is expressed and anchored in the cell wall with the FLAG-tag lying extracellularly and the His-tag lying intracellularly.

Development of Malaria Antigen Specific Antibodies in Mice Immunised with Transfected HEK Cells The high-expressing cell pool of PFF0620c-HEK was used to immunise NMRI mice. Mice received intravenous injections of $10^6$ cells on three consecutive days and another suite of three daily injections two weeks later. Development of serum antibody titres was analysed by flow cytometry comparing immune-staining of the transfectant with that of non-transfected HEK cells. The fluorescence intensity observed with the transfectant was fourfold higher than that of non-transfected control HEK cells. This indicated that the mice had mounted an antibody response against the malaria antigen expressed on the surface of the transfected HEK cells.

Spleen cells of mice immunised with the transfected HEK cells were fused with PAI myeloma cells to generate B cell hybridoma. Fused cells were distributed in microtitre culture plate wells. To identify hybridoma cells that produce PFF0620c-specific antibodies a two-step screening procedure was used that completely obviates the requirement for purified recombinant proteins. First all culture wells were tested for IgG production by ELISA. Between 18 and 29%, of the tested wells were positive. In a second step all wells positive for IgG production were screened for antibody binding to transfected cells by IFA. Transfected and non-transfected HEK cells spotted onto multiwell glass-slides were stained with individual hybridoma supernatants and analysed by fluorescence microscopy (FIG. 4). Non-transfected HEK cells served as a negative control for each sample. Numerous clones positive on the transfected cells were also positive on non-transfected cells. However, the fusion yielded also numerous wells containing antibodies strongly reactive with the transfectant but not reactive with untransfected HEK cells. All other antibodies were specific for the transfected cells used for immunisation and did not stain control transfectants. From wells of this category, 17 hybridoma clones were derived by recloning from the PFF0620c-fusion.

The specificity of the monoclonal antibodies was further confirmed by Western blot analysis (FIG. 5). 16 of the mAbs stained the corresponding recombinant protein in the lysate of the transfectant used for immunisation, but not in lysates of control transfected or untransfected HEK cells.

PFD1130w-Specific Monoclonal Antibodies Inhibit Parasite Growth In Vivo

We evaluated the in vivo parasite inhibitory activity of anti-PFD1130w mAbs in a *P. falciparum* SCID mouse model. The anti-PFD1130w mAbs were produced using the same methods and vectors that were used for the generation of the mAbs against *P. falciparum* PFF0620c (see methods section below). This model uses non-myelodepleted NOD-scid IL2Rnull mice engrafted with human erythrocytes in order to allow the growth of *P. falciparum*. Groups of three mice with a parasitemia of 0.58±0.14% were injected once with 2.5 mg anti-PFD1130w c12 mAb, 0.5 mg anti-PFD1130w c12 mAb or 2.5 mg isotype/subclass control mAb per mouse, respectively. Parasitemia of all mice was monitored for the next six days. While the parasitemia in mice that had received PBS only or the control mAb increased continuously, reaching 11.3±0.8% after six days, parasitemia of mice that received 0.5 mg anti-PFD1130w c12 mAb increased to a much lower extent, reaching 5.6±1.3% after six days. Parasitemia of mice receiving 2.5 mg anti-PFD1130w c12 mAb stayed low till the end of the experiment (1.4±0.3% on day 6). The difference in parasitemia after 6 days compared to the negative control group was highly significant (two-sided t-test; P<0.0001) (FIG. 6).

The fact that anti-PFD1130w mAbs inhibit parasite growth in vivo indicates the power of the described entirely cell-based technology to generate mAbs that bind the endogenous protein in its native context.

Methods

Construction of Plasmids and Transformation

A double-stranded oligonucleotide encoding the secretion signal sequence of bee-venom melittin was ligated to NheI digested pcDNA3.1(+) (Invitrogen) resulting in plasmid pcDNA3.1_BVM, with a single NheI site retained 3' of the signal sequence. A mouse glycophorin cytoplasmic and transmembrane domain cDNA was obtained by rtPCR (Invitrogen SuperScript III First Strand Synthesis kit and Roche Expand High Fidelity PCR System) using RNA extracted from bone marrow as a template. The resulting PCR amplicon being cloned into a pCR2.1 cloning vector. Primers to mouse glycophorin contained a 5' NotI site and 3' histidine tag followed by a stop codon and EagI site. The glycophorin-6His fragment was excised with EagI and ligated to NotI-digested pcDNA3.1_BVM resulting in plasmid pcDNA3.1_BVM_GP with the pcDNA3.1 NotI site preserved at the 5' end of the glycophorin sequence. To create the finished expression vector (pANITA2) a double-stranded oligonucleotide was ligated into NotI-digested pcDNA3.1_BVM_GP encoding a Flag-tag flanked by short linker sequences and resulting in a unique NotI site to the 5' side of the Flag-tag.

Rat TMEM27 extracellular domain (aa 15-130 of Seq. Id. No. 9); a predicted extracellular domain of *P. falciparum* gene PFF0620C (aa 21-353 of Seq. Id. No. 11) and human ABCA1 N-terminal extracellular domain (aa 43-640 of Seq. Id. No. 7) cDNA sequences were synthesised with optimisation of codon usage to give high expression in mammalian cell culture. The genes were ligated into the unique NheI and NotI sites of the pANITA2 vector and the sequence of the vectors confirmed by DNA sequencing. The resulting plasmids are hereafter referred to as pA-NITA2-TMEM27; pANITA2-PFF0620C or pANITA2-ABCA1 respectively.

In pANITA3.1 and pANITA3.3, the native pcDNA3.1 XbaI and XhoI sites were also removed by site-directed mutagenesis. The features of the multiple cloning sites and fusion-protein-coding sequences are shown in the table 1 below, with numbering from the insert start.

Armenian hamster glycophorin sequence was determined by PCR-cloning and nucleotide sequencing using the Chinese hamster glycophorin sequence as a guide for primer design and cDNA generated from Armenian hamster bone-marrow RNA preparations. The following sequences are depicted in table 1: pANITA2 with Kozak sequence=Seq. Id. No. 15, pANITA3.1=Seq. Id. No. 13 and pANITA3.3=Seq. Id. No. 14.

TABLE 1

Comparison of expression vectors

| Vector element | pANITA2 | pANITA3.1 | pANITA3.3 |
|---|---|---|---|
| Kozak sequence | 1-12 | 1-12 | 1-12 |
| Bee venom melittin signal sequence | 9-72 | 9-72 | 9-72 |
| Unique NheI restriction site | 70-75 | 70-75 | 70-75 |
| Unique KpnI restriction site | 82-87 | 82-87 | 82-87 |
| Unique BamHI restriction site | 94-99 | 94-99 | 94-99 |
| Unique EcoRI restriction site | 106-111 | 106-111 | 106-111 |
| Unique EcoRV restriction site | 112-117 | 112-117 | 112-117 |
| Unique XbaI restriction site | — | 118-123 | 118-123 |
| Unique NotI restriction site | 124-131 | 124-131 | 124-131 |
| Flag tag/Enterokinase cleavage site | 133-156 | 133-156 | 133-156 |
| Unique HindIII restriction site | — | 154-159 | 154-159 |
| Mouse glycophorin membrane anchor | 172-369 | 163-369 | — |
| Armenian hamster glycophorin membrane anchor | — | — | 178-375 |
| 6-His tag | 382-399 | 382-399 | 388-405 |
| Stop codons | 400-405 | 400-405 | 406-411 |

Establishment of HEK 293 Cell Lines Stably Expressing PFF0620C, TMEM27 or ABCA1 Domains.

293 HEK cells were transfected with pANITA2-TMEM27; pANITA2-PFF0620C or pA-NITA2-ABCA1 using JetPEI™ (PolyPlus) transfection reagent following the manufacturer's protocol. Antibiotic selection was started 48 h after transfection. The selection medium containing 500 ug/ml of Geneticin (Gibco) was exchanged every 3-4 days. After non-antibiotic resistant cells had died off and resistant cells started growing normally, a high-expressing pool was generated by FACS. Cells were dissociated with enzyme-free dissociation buffer (Cell dissociation buffer enzyme-free Hanks'-based, Gibco), washed with blocking buffer (PBS containing 3% BSA). The cells were then incubated with 200 μl of 100 μg/ml anti-FLAG mAb=FLAG-27 diluted in blocking buffer for 15 min on ice. The cells were then washed with blocking buffer and incubated with 200 μl of 100 μg/ml FITC-conjugated goat anti-mouse IgG antibodies (RAM/IgG(H+L)/FITC, Nordic Immunological Laboratories) diluted in blocking buffer for 15 min on ice. After a final wash the labelled cells were analysed and sorted using a BD FACSAria running FACSDiva software. All analyses were performed using appropriate scatter gates to exclude cellular debris and aggregates. Gating settings were set to collect highly labelled cells. Post-sorting, the cells were collected in culture medium with 20% FCS and plated in 35 mm wells.

Immunofluorescence Staining of Living HEK Cells

For immunofluorescence staining of live HEK cells chamber slides (4-well chamber-slide, Lab-Tek™, Nunc™) were used. Wells were coated with 100 mg/l poly-D-lysine in $H_2O$ in a humid box at room temperature over night. After washing the wells three times with sterile $H_2O$, 40,000 cells were seeded per well. Three days later the immunostaining was performed by incubating the wells with 500 μl of an appropriate mAb diluted in serum-free culture medium for 30 min on ice. After washing two times with serum-free culture medium 500 μl of 100 μg/ml FITC-conjugated goat anti-mouse IgG antibodies (RAM/IgG(H+L)/FITC, Nordic Immunological Laboratories) diluted in serum-free culture medium were added to the wells and incubated for 30 min on ice. Finally, the wells were rinsed twice with serum-free culture medium and once with DPBS (Dulbecco's Phosphate-Buffered Saline containing calcium, Gibco). The slides were mounted with mounting solution containing DAPI (ProLong® Gold antifade reagent with DAPI, Invitrogen) and covered with a coverslip Stainings were assessed as described above.

Immunisation of Mice

NMRI mice were immunised by intravenous injections of $10^6$ stably transfected HEK cells. Cells were thawed, washed and resuspended in 0.9% NaCl. Injections were accomplished on three consecutive days and after two weeks again on three consecutive days. After the boost, blood was collected and the serum was tested for the presence of anti-PFF0620C antibodies by IFA using stably transfected 293 HEK cells.

Animals with serum strongly reactive with expressing cells were selected for fusion. These received a final injection of $10^6$ cells two and one day before the fusion. Mice were sacrificed and the spleen was removed. Spleen cells were harvested by trituration under sterile conditions and fused with the myeloma cell partner (PAI mouse myeloma cells, derived from P-3X63-Ag8) using polyethylene glycol 1500 (Roche Diagnostics). The fusion mix was plated into multiwell plates and hybridomas were selected by growing in HAT medium supplemented with culture supernatant of mouse macrophages P388. Wells were screened for specific IgG production between 2-3 weeks post-fusion by ELISA and IFA as described below. Cells from wells positive in initial screens were cloned by limiting dilution to obtain monoclonal populations.

IgG ELISA Screen

Maxisorp™ plates (Nunc) were coated overnight at 4° C. in a humid box with 100 μl of 5 μg/ml goat anti-mouse IgG (γ-chain specific) mAb (Sigma) diluted in PBS. After two washings with PBS containing 0.05% Tween-20, wells were blocked with blocking buffer (50 mM Tris, 140 mM NaCl, 5 mM EDTA, 0.05% NONidet P40, 0.25% gelatine, 1% BSA) for 1 h at 37° C. and afterwards washed two times. 50 μl hybridoma supernatants were added to the wells and incubated for 1 h at 37° C. After washing 4 times, plates were incubated with 50 μl horseradish peroxidase-conjugated goat anti-mouse IgG (γ-chain specific) (Sigma) diluted 1:1000 in blocking buffer for 1 h at room-temperature in a humid box in the dark. After washing 4 times, TMB peroxidase substrate solution was added and the colour change monitored.

Antibody Production and Characterisation

Identification of antibody isotypes was performed using a Mouse Monoclonal Antibody Isotyping Kit (ISO2, Sigma). For large-scale mAb production hybridoma cell lines were cultured in 500 ml roller-bottles (Corning). MAbs were purified by affinity chromatography using protein A or protein G Sepharose.

DNA and Protein Sequences

| Gene/Protein name | Species | Description | Seq. Id. No. |
|---|---|---|---|
| Glycophorin A | Mouse | Transmembrane + cytoplasmic domain of glycophorin A | 1 |
| Melittin | Bee | Secretion signal of bee venom melittin | 2 |
| Flag tag | — | Flag tag | 3 |
| His tag | — | His tag | 4 |
| Expression vector pANITA2 (without | — | Expression vector sequence comprising secretion signal of bee venom melittin, cloning site for a | 5 |

-continued

| Gene/Protein name | Species | Description | Seq. Id. No. |
|---|---|---|---|
| Kozak sequence) | | protein to be expressed and transmembrane domain of mouse glycophorin A | |
| ABCA1 | Human | DNA encoding human ABCA1 protein | 6 |
| ABCA1 | Human | ABCA1 protein | 7 |
| TMEM27 | Rat | DNA encoding rat TMEM27 | 8 |
| TMEM27 | Rat | TMEM27 protein | 9 |
| PFF0620C | *Plasmodium falciparum* | DNA encoding 3D7 protein | 10 |
| PFF0620C | *Plasmodium falciparum* | 3D7 protein | 11 |
| Glycophorin A | Armenian hamster | Transmembrane + cytoplasmic domain of glycophorin A | 12 |
| Expression vector pANITA3.1 | — | Expression vector sequence comprising secretion signal of bee venom melittin, cloning site for a protein to be expressed and transmembrane domain of mouse glycophorin A | 13 |
| Expression vector pANITA3.3 | — | Expression vector sequence comprising secretion signal of bee venom melittin, cloning site for a protein to be expressed and transmembrane domain of Armenian hamster glycophorin A | 14 |
| Expression vector pANITA2 with Kozak sequence (nt 1-12) | — | Expression vector sequence comprising secretion signal of bee venom melittin, cloning site for a protein to be expressed and transmembrane domain of mouse glycophorin A | 15 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A nucleic acid expression vector for cell-surface expression of proteins comprising in order a polynucleotide sequence comprising a sequence encoding a secretion signal peptide, a cloning site for inserting a polynucleotide sequence encoding a protein to be expressed and a polynucleotide sequence comprising a sequence encoding a transmembrane domain of glycophorin, wherein the vector comprises a polynucleotide sequence selected from the group consisting of SEQ ID NO:5, SEQ ID NO:13, SEQ ID NO:14, and SEQ ID NO:15.

2. The nucleic acid vector of claim 1, wherein the protein to be expressed is a membrane associated protein.

3. A eukaryotic cell comprising the vector of claim 1.

4. The eukaryotic cell of claim 3, wherein the eukaryotic cell is a mammalian cell.

5. The eukaryotic cell of claim 3, wherein the eukaryotic cell is an HEK cell.

6. A method for expressing a protein suitable for antibody generation, the method comprising culturing the cell of claim 3 under conditions suitable for expressing the protein.

7. A method for the generation of monoclonal antibodies against a specific protein comprising the steps:
   a) immunization of a non-human animal with cells expressing on its cell surfaces the specific protein using the vector of claim 1,
   b) isolating spleen cells of the non-human animals of step a),
   c) fusing the spleen cells of step b) with myeloma cells to generate B cell hybridomas and
   d) identification of B cell hybridomas expressing antibodies directed against the specific protein.

8. The method of claim 7, wherein the non-human animal is a mouse or hamster.

* * * * *

SEQUENCE LISTING

```
<160> NUMBER OF SEQ ID NOS: 15

<210> SEQ ID NO 1
<211> LENGTH: 66
<212> TYPE: PRT
<213> ORGANISM: Mus musculus

<400> SEQUENCE: 1

His Asp Phe Pro Ala Leu Val Met Ile Leu Ile Ile Leu Gly Val Met
1               5                   10                  15

Ala Gly Ile Ile Gly Thr Ile Leu Leu Ile Ser Tyr Cys Ile Ser Arg
            20                  25                  30

Met Thr Lys Lys Ser Ser Val Asp Ile Gln Ser Pro Glu Gly Gly Asp
        35                  40                  45

Asn Ser Val Pro Leu Ser Ser Ile Glu Gln Thr Pro Asn Glu Glu Ser
    50                  55                  60

Ser Asn
65

<210> SEQ ID NO 2
<211> LENGTH: 21
<212> TYPE: PRT
<213> ORGANISM: Apis mellifera

<400> SEQUENCE: 2

Met Lys Phe Leu Val Asn Val Ala Leu Val Phe Met Val Val Tyr Ile
1               5                   10                  15

Ser Phe Ile Tyr Ala
            20

<210> SEQ ID NO 3
<211> LENGTH: 8
<212> TYPE: PRT
<213> ORGANISM: Artificial Sequence
<220> FEATURE:
<223> OTHER INFORMATION: FLAG tag
```

<400> SEQUENCE: 3

Asp Tyr Lys Asp Asp Asp Lys
1               5

<210> SEQ ID NO 4
<211> LENGTH: 10
<212> TYPE: PRT
<213> ORGANISM: Artificial Sequence
<220> FEATURE:
<223> OTHER INFORMATION: His Tag

<400> SEQUENCE: 4

Val Ser Gly Gly His His His His His His
1               5                   10

<210> SEQ ID NO 5
<211> LENGTH: 390
<212> TYPE: DNA
<213> ORGANISM: Artificial Sequence
<220> FEATURE:
<223> OTHER INFORMATION: Expression construct

<400> SEQUENCE: 5

```
atgaagttcc tggtgaatgt ggccttggtg ttcatggtgg tgtacatcag cttcatctac      60
gctagcctta agggtaccga gctcggatcc actagtgaat tcgatatcga cgtcgcggcc     120
gctgactaca agacgatga cgacaagagc cctagggccg cacacgattt tcctgcacta     180
gtgatgatac tcataatttt gggcgtgatg gcaggatta tcggaactat ccttcttatc     240
tcttactgta tcagccgaat gacaaagaaa agttcagttg acatccaatc tcctgagggt     300
ggtgacaaca gtgtgccttt gagttctatt gagcagactc ctaatgaaga gtcctccaat     360
gttagcggcg gccatcacca tcaccatcac                                      390
```

<210> SEQ ID NO 6
<211> LENGTH: 7140
<212> TYPE: DNA
<213> ORGANISM: Homo sapiens
<220> FEATURE:
<221> NAME/KEY: CDS
<222> LOCATION: (314)..(7099)

<400> SEQUENCE: 6

```
gtaattgcga gcgagagtga gtggggccgg gacccgcaga gccgagccga cccttctctc      60
ccgggctgcg gcagggcagg gcggggagct ccgcgcacca acagagccgg ttctcagggc     120
gctttgctcc ttgttttttc cccggttctg ttttctcccc ttctccggaa ggcttgtcaa     180
ggggtaggag aaagagacgc aaacacaaaa gtggaaaaca gttaatgacc agccacggcg     240
tccctgctgt gagctctggc cgctgccttc cagggctccc gagccacacg ctggggtgc     300 tggctgaggg aac atg gct tgt tgg cct cag ctg agg ttg ctg ctg tgg        349
              Met Ala Cys Trp Pro Gln Leu Arg Leu Leu Leu Trp
                1               5                   10 aag aac ctc act ttc aga aga aga caa aca tgt cag ctg ctg ctg gaa        397
Lys Asn Leu Thr Phe Arg Arg Arg Gln Thr Cys Gln Leu Leu Leu Glu
        15                  20                  25 gtg gcc tgg cct cta ttt atc ttc ctg atc ctg atc tct gtt cgg ctg        445
Val Ala Trp Pro Leu Phe Ile Phe Leu Ile Leu Ile Ser Val Arg Leu
    30                  35                  40 agc tac cca ccc tat gaa caa cat gaa tgc cat ttt cca aat aaa gcc        493
Ser Tyr Pro Pro Tyr Glu Gln His Glu Cys His Phe Pro Asn Lys Ala
45                  50                  55                  60
```

```
atg ccc tct gca gga aca ctt cct tgg gtt cag ggg att atc tgt aat    541
Met Pro Ser Ala Gly Thr Leu Pro Trp Val Gln Gly Ile Ile Cys Asn
             65                  70                  75 gcc aac aac ccc tgt ttc cgt tac ccg act cct ggg gag gct ccc gga    589
Ala Asn Asn Pro Cys Phe Arg Tyr Pro Thr Pro Gly Glu Ala Pro Gly
         80                  85                  90 gtt gtt gga aac ttt aac aaa tcc att gtg gct cgc ctg ttc tca gat    637
Val Val Gly Asn Phe Asn Lys Ser Ile Val Ala Arg Leu Phe Ser Asp
     95                 100                 105 gct cgg agg ctt ctt tta tac agc cag aaa gac acc agc atg aag gac    685
Ala Arg Arg Leu Leu Leu Tyr Ser Gln Lys Asp Thr Ser Met Lys Asp
    110                 115                 120 atg cgc aaa gtt ctg aga aca tta cag cag atc aag aaa tcc agc tca    733
Met Arg Lys Val Leu Arg Thr Leu Gln Gln Ile Lys Lys Ser Ser Ser
125                 130                 135                 140 aac ttg aag ctt caa gat ttc ctg gtg gac aat gaa acc ttc tct ggg    781
Asn Leu Lys Leu Gln Asp Phe Leu Val Asp Asn Glu Thr Phe Ser Gly
                145                 150                 155 ttc ctg tat cac aac ctc tct ctc cca aag tct act gtg gac aag atg    829
Phe Leu Tyr His Asn Leu Ser Leu Pro Lys Ser Thr Val Asp Lys Met
            160                 165                 170 ctg agg gct gat gtc att ctc cac aag gta ttt ttg caa ggc tac cag    877
Leu Arg Ala Asp Val Ile Leu His Lys Val Phe Leu Gln Gly Tyr Gln
        175                 180                 185 tta cat ttg aca agt ctg tgc aat gga tca aaa tca gaa gag atg att    925
Leu His Leu Thr Ser Leu Cys Asn Gly Ser Lys Ser Glu Glu Met Ile
    190                 195                 200 caa ctt ggt gac caa gaa gtt tct gag ctt tgt ggc cta cca agg gag    973
Gln Leu Gly Asp Gln Glu Val Ser Glu Leu Cys Gly Leu Pro Arg Glu
205                 210                 215                 220 aaa ctg gct gca gca gag cga gta ctt cgt tcc aac atg gac atc ctg   1021
Lys Leu Ala Ala Ala Glu Arg Val Leu Arg Ser Asn Met Asp Ile Leu
                225                 230                 235 aag cca atc ctg aga aca cta aac tct aca tct ccc ttc ccg agc aag   1069
Lys Pro Ile Leu Arg Thr Leu Asn Ser Thr Ser Pro Phe Pro Ser Lys
            240                 245                 250 gag ctg gct gaa gcc aca aaa aca ttg ctg cat agt ctt ggg act ctg   1117
Glu Leu Ala Glu Ala Thr Lys Thr Leu Leu His Ser Leu Gly Thr Leu
        255                 260                 265 gcc cag gag ctg ttc agc atg aga agc tgg agt gac atg cga cag gag   1165
Ala Gln Glu Leu Phe Ser Met Arg Ser Trp Ser Asp Met Arg Gln Glu
    270                 275                 280 gtg atg ttt ctg acc aat gtg aac agc tcc agc tcc tcc acc caa atc   1213
Val Met Phe Leu Thr Asn Val Asn Ser Ser Ser Ser Thr Gln Ile
285                 290                 295                 300 tac cag gct gtg tct cgt att gtc tgc ggg cat ccc gag gga ggg ggg   1261
Tyr Gln Ala Val Ser Arg Ile Val Cys Gly His Pro Glu Gly Gly Gly
                305                 310                 315 ctg aag atc aag tct ctc aac tgg tat gag gac aac aac tac aaa gcc   1309
Leu Lys Ile Lys Ser Leu Asn Trp Tyr Glu Asp Asn Asn Tyr Lys Ala
            320                 325                 330 ctc ttt gga ggc aat ggc act gag gaa gat gct gaa acc ttc tat gac   1357
Leu Phe Gly Gly Asn Gly Thr Glu Glu Asp Ala Glu Thr Phe Tyr Asp
        335                 340                 345 aac tct aca act cct tac tgc aat gat ttg atg aag aat ttg gag tct   1405
Asn Ser Thr Thr Pro Tyr Cys Asn Asp Leu Met Lys Asn Leu Glu Ser
    350                 355                 360 agt cct ctt tcc cgc att atc tgg aaa gct ctg aag ccg ctg ctc gtt   1453
Ser Pro Leu Ser Arg Ile Ile Trp Lys Ala Leu Lys Pro Leu Leu Val
```

```
       365                 370                 375                 380
ggg aag atc ctg tat aca cct gac act cca gcc aca agg cag gtc atg      1501
Gly Lys Ile Leu Tyr Thr Pro Asp Thr Pro Ala Thr Arg Gln Val Met
                    385                 390                 395 gct gag gtg aac aag acc ttc cag gaa ctg gct gtg ttc cat gat ctg      1549
Ala Glu Val Asn Lys Thr Phe Gln Glu Leu Ala Val Phe His Asp Leu
                400                 405                 410 gaa ggc atg tgg gag gaa ctc agc ccc aag atc tgg acc ttc atg gag      1597
Glu Gly Met Trp Glu Glu Leu Ser Pro Lys Ile Trp Thr Phe Met Glu
            415                 420                 425 aac agc caa gaa atg gac ctt gtc cgg atg ctg ttg gac agc agg gac      1645
Asn Ser Gln Glu Met Asp Leu Val Arg Met Leu Leu Asp Ser Arg Asp
        430                 435                 440 aat gac cac ttt tgg gaa cag cag ttg gat ggc tta gat tgg aca gcc      1693
Asn Asp His Phe Trp Glu Gln Gln Leu Asp Gly Leu Asp Trp Thr Ala
445                 450                 455                 460 caa gac atc gtg gcg ttt ttg gcc aag cac cca gag gat gtc cag tcc      1741
Gln Asp Ile Val Ala Phe Leu Ala Lys His Pro Glu Asp Val Gln Ser
                    465                 470                 475 agt aat ggt tct gtg tac acc tgg aga gaa gct ttc aac gag act aac      1789
Ser Asn Gly Ser Val Tyr Thr Trp Arg Glu Ala Phe Asn Glu Thr Asn
                480                 485                 490 cag gca atc cgg acc ata tct cgc ttc atg gag tgt gtc aac ctg aac      1837
Gln Ala Ile Arg Thr Ile Ser Arg Phe Met Glu Cys Val Asn Leu Asn
            495                 500                 505 aag cta gaa ccc ata gca aca gaa gtc tgg ctc atc aac aag tcc atg      1885
Lys Leu Glu Pro Ile Ala Thr Glu Val Trp Leu Ile Asn Lys Ser Met
        510                 515                 520 gag ctg ctg gat gag agg aag ttc tgg gct ggt att gtg ttc act gga      1933
Glu Leu Leu Asp Glu Arg Lys Phe Trp Ala Gly Ile Val Phe Thr Gly
525                 530                 535                 540 att act cca ggc agc att gag ctg ccc cat cat gtc aag tac aag atc      1981
Ile Thr Pro Gly Ser Ile Glu Leu Pro His His Val Lys Tyr Lys Ile
                    545                 550                 555 cga atg gac att gac aat gtg gag agg aca aat aaa atc aag gat ggg      2029
Arg Met Asp Ile Asp Asn Val Glu Arg Thr Asn Lys Ile Lys Asp Gly
                560                 565                 570 tac tgg gac cct ggt cct cga gct gac ccc ttt gag gac atg cgg tac      2077
Tyr Trp Asp Pro Gly Pro Arg Ala Asp Pro Phe Glu Asp Met Arg Tyr
            575                 580                 585 gtc tgg ggg ggc ttc gcc tac ttg cag gat gtg gtg gag cag gca atc      2125
Val Trp Gly Gly Phe Ala Tyr Leu Gln Asp Val Val Glu Gln Ala Ile
        590                 595                 600 atc agg gtg ctg acg ggc acc gag aag aaa act ggt gtc tat atg caa      2173
Ile Arg Val Leu Thr Gly Thr Glu Lys Lys Thr Gly Val Tyr Met Gln
605                 610                 615                 620 cag atg ccc tat ccc tgt tac gtt gat gac atc ttt ctg cgg gtg atg      2221
Gln Met Pro Tyr Pro Cys Tyr Val Asp Asp Ile Phe Leu Arg Val Met
                    625                 630                 635 agc cgg tca atg ccc ctc ttc atg acg ctg gcc tgg att tac tca gtg      2269
Ser Arg Ser Met Pro Leu Phe Met Thr Leu Ala Trp Ile Tyr Ser Val
                640                 645                 650 gct gtg atc atc aag ggc atc gtg tat gag aag gag gca cgg ctg aaa      2317
Ala Val Ile Ile Lys Gly Ile Val Tyr Glu Lys Glu Ala Arg Leu Lys
            655                 660                 665 gag acc atg cgg atc atg ggc ctg gac aac agc atc ctc tgg ttt agc      2365
Glu Thr Met Arg Ile Met Gly Leu Asp Asn Ser Ile Leu Trp Phe Ser
        670                 675                 680 tgg ttc att agt agc ctc att cct ctt ctt gtg agc gct ggc ctg cta      2413
```

-continued

```
                Trp Phe Ile Ser Ser Leu Ile Pro Leu Leu Val Ser Ala Gly Leu Leu
                685                 690                 695                 700 gtg gtc atc ctg aag tta gga aac ctg ctg ccc tac agt gat ccc agc              2461
Val Val Ile Leu Lys Leu Gly Asn Leu Leu Pro Tyr Ser Asp Pro Ser
                    705                 710                 715 gtg gtg ttt gtc ttc ctg tcc gtg ttt gct gtg gtg aca atc ctg cag              2509
Val Val Phe Val Phe Leu Ser Val Phe Ala Val Val Thr Ile Leu Gln
                720                 725                 730 tgc ttc ctg att agc aca ctc ttc tcc aga gcc aac ctg gca gca gcc              2557
Cys Phe Leu Ile Ser Thr Leu Phe Ser Arg Ala Asn Leu Ala Ala Ala
            735                 740                 745 tgt ggg ggc atc atc tac ttc acg ctg tac ctg ccc tac gtc ctg tgt              2605
Cys Gly Gly Ile Ile Tyr Phe Thr Leu Tyr Leu Pro Tyr Val Leu Cys
        750                 755                 760 gtg gca tgg cag gac tac gtg ggc ttc aca ctc aag atc ttc gct agc              2653
Val Ala Trp Gln Asp Tyr Val Gly Phe Thr Leu Lys Ile Phe Ala Ser
765                 770                 775                 780 ctg ctg tct cct gtg gct ttt ggg ttt ggc tgt gag tac ttt gcc ctt              2701
Leu Leu Ser Pro Val Ala Phe Gly Phe Gly Cys Glu Tyr Phe Ala Leu
                    785                 790                 795 ttt gag gag cag ggc att gga gtg cag tgg gac aac ctg ttt gag agt              2749
Phe Glu Glu Gln Gly Ile Gly Val Gln Trp Asp Asn Leu Phe Glu Ser
                800                 805                 810 cct gtg gag gaa gat ggc ttc aat ctc acc act tcg gtc tcc atg atg              2797
Pro Val Glu Glu Asp Gly Phe Asn Leu Thr Thr Ser Val Ser Met Met
            815                 820                 825 ctg ttt gac acc ttc ctc tat ggg gtg atg acc tgg tac att gag gct              2845
Leu Phe Asp Thr Phe Leu Tyr Gly Val Met Thr Trp Tyr Ile Glu Ala
        830                 835                 840 gtc ttt cca ggc cag tac gga att ccc agg ccc tgg tat ttt cct tgc              2893
Val Phe Pro Gly Gln Tyr Gly Ile Pro Arg Pro Trp Tyr Phe Pro Cys
845                 850                 855                 860 acc aag tcc tac tgg ttt ggc gag gaa agt gat gag aag agc cac cct              2941
Thr Lys Ser Tyr Trp Phe Gly Glu Glu Ser Asp Glu Lys Ser His Pro
                    865                 870                 875 ggt tcc aac cag aag aga ata tca gaa atc tgc atg gag gag gaa ccc              2989
Gly Ser Asn Gln Lys Arg Ile Ser Glu Ile Cys Met Glu Glu Glu Pro
                880                 885                 890 acc cac ttg aag ctg ggc gtg tcc att cag aac ctg gta aaa gtc tac              3037
Thr His Leu Lys Leu Gly Val Ser Ile Gln Asn Leu Val Lys Val Tyr
            895                 900                 905 cga gat ggg atg aag gtg gct gtc gat ggc ctg gca ctg aat ttt tat              3085
Arg Asp Gly Met Lys Val Ala Val Asp Gly Leu Ala Leu Asn Phe Tyr
        910                 915                 920 gag ggc cag atc acc tcc ttc ctg ggc cac aat gga gcg ggg aag acg              3133
Glu Gly Gln Ile Thr Ser Phe Leu Gly His Asn Gly Ala Gly Lys Thr
925                 930                 935                 940 acc acc atg tca atc ctg acc ggg ttg ttc ccc ccg acc tcg ggc acc              3181
Thr Thr Met Ser Ile Leu Thr Gly Leu Phe Pro Pro Thr Ser Gly Thr
                    945                 950                 955 gcc tac atc ctg gga aaa gac att cgc tct gag atg agc acc atc cgg              3229
Ala Tyr Ile Leu Gly Lys Asp Ile Arg Ser Glu Met Ser Thr Ile Arg
                960                 965                 970 cag aac ctg ggg gtc tgt ccc cag cat aac gtg ctg ttt gac atg ctg              3277
Gln Asn Leu Gly Val Cys Pro Gln His Asn Val Leu Phe Asp Met Leu
            975                 980                 985 act gtc gaa gaa cac atc tgg ttc tat gcc cgc ttg  aaa ggg ctc tct             3325
Thr Val Glu Glu His Ile Trp Phe Tyr Ala Arg Leu Lys Gly Leu Ser
        990                 995                 1000
```

| | | |
|---|---|---|
| gag aag cac gtg aag gcg gag atg gag cag atg gcc ctg gat gtt<br>Glu Lys His Val Lys Ala Glu Met Glu Gln Met Ala Leu Asp Val<br>1005                    1010                        1015 | 3370 |
| ggt ttg cca tca agc aag ctg aaa agc aaa aca agc cag ctg tca<br>Gly Leu Pro Ser Ser Lys Leu Lys Ser Lys Thr Ser Gln Leu Ser<br>1020                    1025                        1030 | 3415 |
| ggt gga atg cag aga aag cta tct gtg gcc ttg gcc ttt gtc ggg<br>Gly Gly Met Gln Arg Lys Leu Ser Val Ala Leu Ala Phe Val Gly<br>1035                    1040                        1045 | 3460 |
| gga tct aag gtt gtc att ctg gat gaa ccc aca gct ggt gtg gac<br>Gly Ser Lys Val Val Ile Leu Asp Glu Pro Thr Ala Gly Val Asp<br>1050                    1055                        1060 | 3505 |
| cct tac tcc cgc agg gga ata tgg gag ctg ctg ctg aaa tac cga<br>Pro Tyr Ser Arg Arg Gly Ile Trp Glu Leu Leu Leu Lys Tyr Arg<br>1065                    1070                        1075 | 3550 |
| caa ggc cgc acc att att ctc tct aca cac cac atg gat gaa gcg<br>Gln Gly Arg Thr Ile Ile Leu Ser Thr His His Met Asp Glu Ala<br>1080                    1085                        1090 | 3595 |
| gac gtc ctg ggg gac agg att gcc atc atc tcc cat ggg aag ctg<br>Asp Val Leu Gly Asp Arg Ile Ala Ile Ile Ser His Gly Lys Leu<br>1095                    1100                        1105 | 3640 |
| tgc tgt gtg ggc tcc tcc ctg ttt ctg aag aac cag ctg gga aca<br>Cys Cys Val Gly Ser Ser Leu Phe Leu Lys Asn Gln Leu Gly Thr<br>1110                    1115                        1120 | 3685 |
| ggc tac tac ctg acc ttg gtc aag aaa gat gtg gaa tcc tcc ctc<br>Gly Tyr Tyr Leu Thr Leu Val Lys Lys Asp Val Glu Ser Ser Leu<br>1125                    1130                        1135 | 3730 |
| agt tcc tgc aga aac agt agt agc act gtg tca tac ctg aaa aag<br>Ser Ser Cys Arg Asn Ser Ser Ser Thr Val Ser Tyr Leu Lys Lys<br>1140                    1145                        1150 | 3775 |
| gag gac agt gtt tct cag agc agt tct gat gct ggc ctg ggc agc<br>Glu Asp Ser Val Ser Gln Ser Ser Ser Asp Ala Gly Leu Gly Ser<br>1155                    1160                        1165 | 3820 |
| gac cat gag agt gac acg ctg acc atc gat gtc tct gct atc tcc<br>Asp His Glu Ser Asp Thr Leu Thr Ile Asp Val Ser Ala Ile Ser<br>1170                    1175                        1180 | 3865 |
| aac ctc atc agg aag cat gtg tct gaa gcc cgg ctg gtg gaa gac<br>Asn Leu Ile Arg Lys His Val Ser Glu Ala Arg Leu Val Glu Asp<br>1185                    1190                        1195 | 3910 |
| ata ggg cat gag ctg acc tat gtg ctg cca tat gaa gct gct aag<br>Ile Gly His Glu Leu Thr Tyr Val Leu Pro Tyr Glu Ala Ala Lys<br>1200                    1205                        1210 | 3955 |
| gag gga gcc ttt gtg gaa ctc ttt cat gag att gat gac cgg ctc<br>Glu Gly Ala Phe Val Glu Leu Phe His Glu Ile Asp Asp Arg Leu<br>1215                    1220                        1225 | 4000 |
| tca gac ctg ggc att tct agt tat ggc atc tca gag acg acc ctg<br>Ser Asp Leu Gly Ile Ser Ser Tyr Gly Ile Ser Glu Thr Thr Leu<br>1230                    1235                        1240 | 4045 |
| gaa gaa ata ttc ctc aag gtg gcc gaa gag agt ggg gtg gat gct<br>Glu Glu Ile Phe Leu Lys Val Ala Glu Glu Ser Gly Val Asp Ala<br>1245                    1250                        1255 | 4090 |
| gag acc tca gat ggt acc ttg cca gca aga cga aac agg cgg gcc<br>Glu Thr Ser Asp Gly Thr Leu Pro Ala Arg Arg Asn Arg Arg Ala<br>1260                    1265                        1270 | 4135 |
| ttc ggg gac aag cag agc tgt ctt cgc ccg ttc act gaa gat gat<br>Phe Gly Asp Lys Gln Ser Cys Leu Arg Pro Phe Thr Glu Asp Asp<br>1275                    1280                        1285 | 4180 |
| gct gct gat cca aat gat tct gac ata gac cca gaa tcc aga gag<br>Ala Ala Asp Pro Asn Asp Ser Asp Ile Asp Pro Glu Ser Arg Glu<br>1290                    1295                        1300 | 4225 |

-continued

| | | | | | | | | | | | | |
|---|---|---|---|---|---|---|---|---|---|---|---|---|
| aca | gac | ttg | ctc | agt | ggg | atg | gat | ggc | aaa | ggg | tcc | tac | cag | gtg | 4270 |
| Thr | Asp | Leu | Leu | Ser | Gly | Met | Asp | Gly | Lys | Gly | Ser | Tyr | Gln | Val | |
| 1305 | | | | | 1310 | | | | | 1315 | | | | | |

```
aca gac ttg ctc agt ggg atg gat ggc aaa ggg tcc tac cag gtg         4270
Thr Asp Leu Leu Ser Gly Met Asp Gly Lys Gly Ser Tyr Gln Val
1305                1310                1315 aaa ggc tgg aaa ctt aca cag caa cag ttt gtg gcc ctt ttg tgg         4315
Lys Gly Trp Lys Leu Thr Gln Gln Gln Phe Val Ala Leu Leu Trp
1320                1325                1330 aag aga ctg cta att gcc aga cgg agt cgg aaa gga ttt ttt gct         4360
Lys Arg Leu Leu Ile Ala Arg Arg Ser Arg Lys Gly Phe Phe Ala
1335                1340                1345 cag att gtc ttg cca gct gtg ttt gtc tgc att gcc ctt gtg ttc         4405
Gln Ile Val Leu Pro Ala Val Phe Val Cys Ile Ala Leu Val Phe
1350                1355                1360 agc ctg atc gtg cca ccc ttt ggc aag tac ccc agc ctg gaa ctt         4450
Ser Leu Ile Val Pro Pro Phe Gly Lys Tyr Pro Ser Leu Glu Leu
1365                1370                1375 cag ccc tgg atg tac aac gaa cag tac aca ttt gtc agc aat gat         4495
Gln Pro Trp Met Tyr Asn Glu Gln Tyr Thr Phe Val Ser Asn Asp
1380                1385                1390 gct cct gag gac acg gga acc ctg gaa ctc tta aac gcc ctc acc         4540
Ala Pro Glu Asp Thr Gly Thr Leu Glu Leu Leu Asn Ala Leu Thr
1395                1400                1405 aaa gac cct ggc ttc ggg acc cgc tgt atg gaa gga aac cca atc         4585
Lys Asp Pro Gly Phe Gly Thr Arg Cys Met Glu Gly Asn Pro Ile
1410                1415                1420 cca gac acg ccc tgc cag gca ggg gag gaa gag tgg acc act gcc         4630
Pro Asp Thr Pro Cys Gln Ala Gly Glu Glu Glu Trp Thr Thr Ala
1425                1430                1435 cca gtt ccc cag acc atc atg gac ctc ttc cag aat ggg aac tgg         4675
Pro Val Pro Gln Thr Ile Met Asp Leu Phe Gln Asn Gly Asn Trp
1440                1445                1450 aca atg cag aac cct tca cct gca tgc cag tgt agc agc gac aaa         4720
Thr Met Gln Asn Pro Ser Pro Ala Cys Gln Cys Ser Ser Asp Lys
1455                1460                1465 atc aag aag atg ctg cct gtg tgt ccc cca ggg gca ggg ggg ctg         4765
Ile Lys Lys Met Leu Pro Val Cys Pro Pro Gly Ala Gly Gly Leu
1470                1475                1480 cct cct cca caa aga aaa caa aac act gca gat atc ctt cag gac         4810
Pro Pro Pro Gln Arg Lys Gln Asn Thr Ala Asp Ile Leu Gln Asp
1485                1490                1495 ctg aca gga aga aac att tcg gat tat ctg gtg aag acg tat gtg         4855
Leu Thr Gly Arg Asn Ile Ser Asp Tyr Leu Val Lys Thr Tyr Val
1500                1505                1510 cag atc ata gcc aaa agc tta aag aac aag atc tgg gtg aat gag         4900
Gln Ile Ile Ala Lys Ser Leu Lys Asn Lys Ile Trp Val Asn Glu
1515                1520                1525 ttt agg tat ggc ggc ttt tcc ctg ggt gtc agt aat act caa gca         4945
Phe Arg Tyr Gly Gly Phe Ser Leu Gly Val Ser Asn Thr Gln Ala
1530                1535                1540 ctt cct ccg agt caa gaa gtt aat gat gcc atc aaa caa atg aag         4990
Leu Pro Pro Ser Gln Glu Val Asn Asp Ala Ile Lys Gln Met Lys
1545                1550                1555 aaa cac cta aag ctg gcc aag gac agt tct gca gat cga ttt ctc         5035
Lys His Leu Lys Leu Ala Lys Asp Ser Ser Ala Asp Arg Phe Leu
1560                1565                1570 aac agc ttg gga aga ttt atg aca gga ctg gac acc aaa aat aat         5080
Asn Ser Leu Gly Arg Phe Met Thr Gly Leu Asp Thr Lys Asn Asn
1575                1580                1585 gtc aag gtg tgg ttc aat aac aag ggc tgg cat gca atc agc tct         5125
Val Lys Val Trp Phe Asn Asn Lys Gly Trp His Ala Ile Ser Ser
```

-continued

| | | |
|---|---|---|
| 1590 | 1595 | 1600 | ttc ctg aat gtc atc aac aat gcc att ctc cgg gcc aac ctg caa    5170
Phe Leu Asn Val Ile Asn Asn Ala Ile Leu Arg Ala Asn Leu Gln
1605                1610                1615 aag gga gag aac cct agc cat tat gga att act gct ttc aat cat    5215
Lys Gly Glu Asn Pro Ser His Tyr Gly Ile Thr Ala Phe Asn His
1620                1625                1630 ccc ctg aat ctc acc aag cag cag ctc tca gag gtg gct ctg atg    5260
Pro Leu Asn Leu Thr Lys Gln Gln Leu Ser Glu Val Ala Leu Met
1635                1640                1645 acc aca tca gtg gat gtc ctt gtg tcc atc tgt gtc atc ttt gca    5305
Thr Thr Ser Val Asp Val Leu Val Ser Ile Cys Val Ile Phe Ala
1650                1655                1660 atg tcc ttc gtc cca gcc agc ttt gtc gta ttc ctg atc cag gag    5350
Met Ser Phe Val Pro Ala Ser Phe Val Val Phe Leu Ile Gln Glu
1665                1670                1675 cgg gtc agc aaa gca aaa cac ctg cag ttc atc agt gga gtg aag    5395
Arg Val Ser Lys Ala Lys His Leu Gln Phe Ile Ser Gly Val Lys
1680                1685                1690 cct gtc atc tac tgg ctc tct aat ttt gtc tgg gat atg tgc aat    5440
Pro Val Ile Tyr Trp Leu Ser Asn Phe Val Trp Asp Met Cys Asn
1695                1700                1705 tac gtt gtc cct gcc aca ctg gtc att atc atc ttc atc tgc ttc    5485
Tyr Val Val Pro Ala Thr Leu Val Ile Ile Ile Phe Ile Cys Phe
1710                1715                1720 cag cag aag tcc tat gtg tcc tcc acc aat ctg cct gtg cta gcc    5530
Gln Gln Lys Ser Tyr Val Ser Ser Thr Asn Leu Pro Val Leu Ala
1725                1730                1735 ctt cta ctt ttg ctg tat ggg tgg tca atc aca cct ctc atg tac    5575
Leu Leu Leu Leu Leu Tyr Gly Trp Ser Ile Thr Pro Leu Met Tyr
1740                1745                1750 cca gcc tcc ttt gtg ttc aag atc ccc agc aca gcc tat gtg gtg    5620
Pro Ala Ser Phe Val Phe Lys Ile Pro Ser Thr Ala Tyr Val Val
1755                1760                1765 ctc acc agc gtg aac ctc ttc att ggc att aat ggc agc gtg gcc    5665
Leu Thr Ser Val Asn Leu Phe Ile Gly Ile Asn Gly Ser Val Ala
1770                1775                1780 acc ttt gtg ctg gag ctg ttc acc gac aat aag ctg aat aat atc    5710
Thr Phe Val Leu Glu Leu Phe Thr Asp Asn Lys Leu Asn Asn Ile
1785                1790                1795 aat gat atc ctg aag tcc gtg ttc ttg atc ttc cca cat ttt tgc    5755
Asn Asp Ile Leu Lys Ser Val Phe Leu Ile Phe Pro His Phe Cys
1800                1805                1810 ctg gga cga ggg ctc atc gac atg gtg aaa aac cag gca atg gct    5800
Leu Gly Arg Gly Leu Ile Asp Met Val Lys Asn Gln Ala Met Ala
1815                1820                1825 gat gcc ctg gaa agg ttt ggg gag aat cgc ttt gtg tca cca tta    5845
Asp Ala Leu Glu Arg Phe Gly Glu Asn Arg Phe Val Ser Pro Leu
1830                1835                1840 tct tgg gac ttg gtg gga cga aac ctc ttc gcc atg gcc gtg gaa    5890
Ser Trp Asp Leu Val Gly Arg Asn Leu Phe Ala Met Ala Val Glu
1845                1850                1855 ggg gtg gtg ttc ttc ctc att act gtt ctg atc cag tac aga ttc    5935
Gly Val Val Phe Phe Leu Ile Thr Val Leu Ile Gln Tyr Arg Phe
1860                1865                1870 ttc atc agg ccc aga cct gta aat gca aag cta tct cct ctg aat    5980
Phe Ile Arg Pro Arg Pro Val Asn Ala Lys Leu Ser Pro Leu Asn
1875                1880                1885 gat gaa gat gaa gat gtg agg cgg gaa aga cag aga att ctt gat    6025

-continued

| | | | | | | | | | | | | |
|---|---|---|---|---|---|---|---|---|---|---|---|---|
| Asp | Glu | Asp | Glu | Asp | Val | Arg | Arg | Glu | Arg | Gln | Arg | Ile | Leu | Asp |
| 1890 | | | | 1895 | | | | | 1900 | | | |

| ggt | gga | ggc | cag | aat | gac | atc | tta | gaa | atc | aag | gag | ttg | acg | aag | | 6070 |
|---|---|---|---|---|---|---|---|---|---|---|---|---|---|---|---|---|
| Gly | Gly | Gly | Gln | Asn | Asp | Ile | Leu | Glu | Ile | Lys | Glu | Leu | Thr | Lys | | |
| 1905 | | | | 1910 | | | | | 1915 | | | | | | | |

| ata | tat | aga | agg | aag | cgg | aag | cct | gct | gtt | gac | agg | att | tgc | gtg | | 6115 |
|---|---|---|---|---|---|---|---|---|---|---|---|---|---|---|---|---|
| Ile | Tyr | Arg | Arg | Lys | Arg | Lys | Pro | Ala | Val | Asp | Arg | Ile | Cys | Val | | |
| 1920 | | | | | 1925 | | | | | 1930 | | | | | | |

| ggc | att | cct | cct | ggt | gag | tgc | ttt | ggg | ctc | ctg | gga | gtt | aat | ggg | | 6160 |
|---|---|---|---|---|---|---|---|---|---|---|---|---|---|---|---|---|
| Gly | Ile | Pro | Pro | Gly | Glu | Cys | Phe | Gly | Leu | Leu | Gly | Val | Asn | Gly | | |
| 1935 | | | | | 1940 | | | | | 1945 | | | | | | |

| gct | gga | aaa | tca | tca | act | ttc | aag | atg | tta | aca | gga | gat | acc | act | | 6205 |
|---|---|---|---|---|---|---|---|---|---|---|---|---|---|---|---|---|
| Ala | Gly | Lys | Ser | Ser | Thr | Phe | Lys | Met | Leu | Thr | Gly | Asp | Thr | Thr | | |
| 1950 | | | | | 1955 | | | | | 1960 | | | | | | |

| gtt | acc | aga | gga | gat | gct | ttc | ctt | aac | aaa | aat | agt | atc | tta | tca | | 6250 |
|---|---|---|---|---|---|---|---|---|---|---|---|---|---|---|---|---|
| Val | Thr | Arg | Gly | Asp | Ala | Phe | Leu | Asn | Lys | Asn | Ser | Ile | Leu | Ser | | |
| 1965 | | | | | 1970 | | | | | 1975 | | | | | | |

| aac | atc | cat | gaa | gta | cat | cag | aac | atg | ggc | tac | tgc | cct | cag | ttt | | 6295 |
|---|---|---|---|---|---|---|---|---|---|---|---|---|---|---|---|---|
| Asn | Ile | His | Glu | Val | His | Gln | Asn | Met | Gly | Tyr | Cys | Pro | Gln | Phe | | |
| 1980 | | | | | 1985 | | | | | 1990 | | | | | | |

| gat | gcc | atc | aca | gag | ctg | ttg | act | ggg | aga | gaa | cac | gtg | gag | ttc | | 6340 |
|---|---|---|---|---|---|---|---|---|---|---|---|---|---|---|---|---|
| Asp | Ala | Ile | Thr | Glu | Leu | Leu | Thr | Gly | Arg | Glu | His | Val | Glu | Phe | | |
| 1995 | | | | | 2000 | | | | | 2005 | | | | | | |

| ttt | gcc | ctt | ttg | aga | gga | gtc | cca | gag | aaa | gaa | gtt | ggc | aag | gtt | | 6385 |
|---|---|---|---|---|---|---|---|---|---|---|---|---|---|---|---|---|
| Phe | Ala | Leu | Leu | Arg | Gly | Val | Pro | Glu | Lys | Glu | Val | Gly | Lys | Val | | |
| 2010 | | | | | 2015 | | | | | 2020 | | | | | | |

| ggt | gag | tgg | gcg | att | cgg | aaa | ctg | ggc | ctc | gtg | aag | tat | gga | gaa | | 6430 |
|---|---|---|---|---|---|---|---|---|---|---|---|---|---|---|---|---|
| Gly | Glu | Trp | Ala | Ile | Arg | Lys | Leu | Gly | Leu | Val | Lys | Tyr | Gly | Glu | | |
| 2025 | | | | | 2030 | | | | | 2035 | | | | | | |

| aaa | tat | gct | ggt | aac | tat | agt | gga | ggc | aac | aaa | cgc | aag | ctc | tct | | 6475 |
|---|---|---|---|---|---|---|---|---|---|---|---|---|---|---|---|---|
| Lys | Tyr | Ala | Gly | Asn | Tyr | Ser | Gly | Gly | Asn | Lys | Arg | Lys | Leu | Ser | | |
| 2040 | | | | | 2045 | | | | | 2050 | | | | | | |

| aca | gcc | atg | gct | ttg | atc | ggc | ggg | cct | cct | gtg | gtg | ttt | ctg | gat | | 6520 |
|---|---|---|---|---|---|---|---|---|---|---|---|---|---|---|---|---|
| Thr | Ala | Met | Ala | Leu | Ile | Gly | Gly | Pro | Pro | Val | Val | Phe | Leu | Asp | | |
| 2055 | | | | | 2060 | | | | | 2065 | | | | | | |

| gaa | ccc | acc | aca | ggc | atg | gat | ccc | aaa | gcc | cgg | cgg | ttc | ttg | tgg | | 6565 |
|---|---|---|---|---|---|---|---|---|---|---|---|---|---|---|---|---|
| Glu | Pro | Thr | Thr | Gly | Met | Asp | Pro | Lys | Ala | Arg | Arg | Phe | Leu | Trp | | |
| 2070 | | | | | 2075 | | | | | 2080 | | | | | | |

| aat | tgt | gcc | cta | agt | gtt | gtc | aag | gag | ggg | aga | tca | gta | gtg | ctt | | 6610 |
|---|---|---|---|---|---|---|---|---|---|---|---|---|---|---|---|---|
| Asn | Cys | Ala | Leu | Ser | Val | Val | Lys | Glu | Gly | Arg | Ser | Val | Val | Leu | | |
| 2085 | | | | | 2090 | | | | | 2095 | | | | | | |

| aca | tct | cat | agt | atg | gaa | gaa | tgt | gaa | gct | ctt | tgc | act | agg | atg | | 6655 |
|---|---|---|---|---|---|---|---|---|---|---|---|---|---|---|---|---|
| Thr | Ser | His | Ser | Met | Glu | Glu | Cys | Glu | Ala | Leu | Cys | Thr | Arg | Met | | |
| 2100 | | | | | 2105 | | | | | 2110 | | | | | | |

| gca | atc | atg | gtc | aat | gga | agg | ttc | agg | tgc | ctt | ggc | agt | gtc | cag | | 6700 |
|---|---|---|---|---|---|---|---|---|---|---|---|---|---|---|---|---|
| Ala | Ile | Met | Val | Asn | Gly | Arg | Phe | Arg | Cys | Leu | Gly | Ser | Val | Gln | | |
| 2115 | | | | | 2120 | | | | | 2125 | | | | | | |

| cat | cta | aaa | aat | agg | ttt | gga | gat | ggt | tat | aca | ata | gtt | gta | cga | | 6745 |
|---|---|---|---|---|---|---|---|---|---|---|---|---|---|---|---|---|
| His | Leu | Lys | Asn | Arg | Phe | Gly | Asp | Gly | Tyr | Thr | Ile | Val | Val | Arg | | |
| 2130 | | | | | 2135 | | | | | 2140 | | | | | | |

| ata | gca | ggg | tcc | aac | ccg | gac | ctg | aag | cct | gtc | cag | gat | ttc | ttt | | 6790 |
|---|---|---|---|---|---|---|---|---|---|---|---|---|---|---|---|---|
| Ile | Ala | Gly | Ser | Asn | Pro | Asp | Leu | Lys | Pro | Val | Gln | Asp | Phe | Phe | | |
| 2145 | | | | | 2150 | | | | | 2155 | | | | | | |

| gga | ctt | gca | ttt | cct | gga | agt | gtt | cta | aaa | gag | aaa | cac | cgg | aac | | 6835 |
|---|---|---|---|---|---|---|---|---|---|---|---|---|---|---|---|---|
| Gly | Leu | Ala | Phe | Pro | Gly | Ser | Val | Leu | Lys | Glu | Lys | His | Arg | Asn | | |
| 2160 | | | | | 2165 | | | | | 2170 | | | | | | |

| atg | cta | caa | tac | cag | ctt | cca | tct | tca | tta | tct | tct | ctg | gcc | agg | | 6880 |
|---|---|---|---|---|---|---|---|---|---|---|---|---|---|---|---|---|
| Met | Leu | Gln | Tyr | Gln | Leu | Pro | Ser | Ser | Leu | Ser | Ser | Leu | Ala | Arg | | |
| 2175 | | | | | 2180 | | | | | 2185 | | | | | | |

-continued

| | | | | | | | | | | |
|---|---|---|---|---|---|---|---|---|---|---|
| ata | ttc | agc | atc | ctc | tcc | cag | agc | aaa | aag | cga | ctc | cac | ata | gaa | 6925 |
| Ile | Phe | Ser | Ile | Leu | Ser | Gln | Ser | Lys | Lys | Arg | Leu | His | Ile | Glu | |
| 2190 | | | | 2195 | | | | | 2200 | | | | | | |

| gac | tac | tct | gtt | tct | cag | aca | aca | ctt | gac | caa | gta | ttt | gtg | aac | 6970 |
| Asp | Tyr | Ser | Val | Ser | Gln | Thr | Thr | Leu | Asp | Gln | Val | Phe | Val | Asn | |
| 2205 | | | | | 2210 | | | | 2215 | | | | | | |

| ttt | gcc | aag | gac | caa | agt | gat | gat | gac | cac | tta | aaa | gac | ctc | tca | 7015 |
| Phe | Ala | Lys | Asp | Gln | Ser | Asp | Asp | Asp | His | Leu | Lys | Asp | Leu | Ser | |
| 2220 | | | | | 2225 | | | | 2230 | | | | | | |

| tta | cac | aaa | aac | cag | aca | gta | gtg | gac | gtt | gca | gtt | ctc | aca | tct | 7060 |
| Leu | His | Lys | Asn | Gln | Thr | Val | Val | Asp | Val | Ala | Val | Leu | Thr | Ser | |
| 2235 | | | | | 2240 | | | | | 2245 | | | | | |

| ttt | cta | cag | gat | gag | aaa | gtg | aaa | gaa | agc | tat | gta | tga | agaatcctgt | 7109 |
| Phe | Leu | Gln | Asp | Glu | Lys | Val | Lys | Glu | Ser | Tyr | Val | | | |
| 2250 | | | | | 2255 | | | | | 2260 | | | | | tcatacgggg tggctgaaag taaagaggaa c    7140

<210> SEQ ID NO 7
<211> LENGTH: 2261
<212> TYPE: PRT
<213> ORGANISM: Homo sapiens

<400> SEQUENCE: 7

Met Ala Cys Trp Pro Gln Leu Arg Leu Leu Leu Trp Lys Asn Leu Thr
1               5                   10                  15

Phe Arg Arg Arg Gln Thr Cys Gln Leu Leu Glu Val Ala Trp Pro
            20                  25                  30

Leu Phe Ile Phe Leu Ile Leu Ile Ser Val Arg Leu Ser Tyr Pro Pro
        35                  40                  45

Tyr Glu Gln His Glu Cys His Phe Pro Asn Lys Ala Met Pro Ser Ala
    50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
        115                 120                 125

Leu Arg Thr Leu Gln Gln Ile Lys Lys Ser Ser Asn Leu Lys Leu
    130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
            180                 185                 190

Ser Leu Cys Asn Gly Ser Lys Ser Glu Glu Met Ile Gln Leu Gly Asp
        195                 200                 205

Gln Glu Val Ser Glu Leu Cys Gly Leu Pro Arg Glu Lys Leu Ala Ala
    210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu

```
                260                 265                 270
Phe Ser Met Arg Ser Trp Ser Asp Met Arg Gln Glu Val Met Phe Leu
            275                 280                 285

Thr Asn Val Asn Ser Ser Ser Thr Gln Ile Tyr Gln Ala Val
290                 295                 300

Ser Arg Ile Val Cys Gly His Pro Glu Gly Gly Leu Lys Ile Lys
305                 310                 315                 320

Ser Leu Asn Trp Tyr Glu Asp Asn Asn Tyr Lys Ala Leu Phe Gly Gly
            325                 330                 335

Asn Gly Thr Glu Glu Asp Ala Glu Thr Phe Tyr Asp Asn Ser Thr Thr
            340                 345                 350

Pro Tyr Cys Asn Asp Leu Met Lys Asn Leu Glu Ser Ser Pro Leu Ser
            355                 360                 365

Arg Ile Ile Trp Lys Ala Leu Lys Pro Leu Leu Val Gly Lys Ile Leu
            370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
            405                 410                 415

Glu Glu Leu Ser Pro Lys Ile Trp Thr Phe Met Glu Asn Ser Gln Glu
            420                 425                 430

Met Asp Leu Val Arg Met Leu Leu Asp Ser Arg Asp Asn Asp His Phe
            435                 440                 445

Trp Glu Gln Gln Leu Asp Gly Leu Asp Trp Thr Ala Gln Asp Ile Val
            450                 455                 460

Ala Phe Leu Ala Lys His Pro Glu Asp Val Gln Ser Ser Asn Gly Ser
465                 470                 475                 480

Val Tyr Thr Trp Arg Glu Ala Phe Asn Glu Thr Asn Gln Ala Ile Arg
            485                 490                 495

Thr Ile Ser Arg Phe Met Glu Cys Val Asn Leu Asn Lys Leu Glu Pro
            500                 505                 510

Ile Ala Thr Glu Val Trp Leu Ile Asn Lys Ser Met Glu Leu Leu Asp
            515                 520                 525

Glu Arg Lys Phe Trp Ala Gly Ile Val Phe Thr Gly Ile Thr Pro Gly
            530                 535                 540

Ser Ile Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
            565                 570                 575

Gly Pro Arg Ala Asp Pro Phe Glu Asp Met Arg Tyr Val Trp Gly Gly
            580                 585                 590

Phe Ala Tyr Leu Gln Asp Val Val Glu Gln Ala Ile Ile Arg Val Leu
            595                 600                 605

Thr Gly Thr Glu Lys Lys Thr Gly Val Tyr Met Gln Gln Met Pro Tyr
            610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
            645                 650                 655

Lys Gly Ile Val Tyr Glu Lys Glu Ala Arg Leu Lys Glu Thr Met Arg
            660                 665                 670

Ile Met Gly Leu Asp Asn Ser Ile Leu Trp Phe Ser Trp Phe Ile Ser
            675                 680                 685
```

```
Ser Leu Ile Pro Leu Leu Val Ser Ala Gly Leu Leu Val Ile Leu
    690                 695                 700

Lys Leu Gly Asn Leu Leu Pro Tyr Ser Asp Pro Ser Val Val Phe Val
705                 710                 715                 720

Phe Leu Ser Val Phe Ala Val Val Thr Ile Leu Gln Cys Phe Leu Ile
            725                 730                 735

Ser Thr Leu Phe Ser Arg Ala Asn Leu Ala Ala Ala Cys Gly Gly Ile
                740                 745                 750

Ile Tyr Phe Thr Leu Tyr Leu Pro Tyr Val Leu Cys Val Ala Trp Gln
            755                 760                 765

Asp Tyr Val Gly Phe Thr Leu Lys Ile Phe Ala Ser Leu Leu Ser Pro
770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ser Val Ser Met Met Leu Phe Asp Thr
                820                 825                 830

Phe Leu Tyr Gly Val Met Thr Trp Tyr Ile Glu Ala Val Phe Pro Gly
            835                 840                 845

Gln Tyr Gly Ile Pro Arg Pro Trp Tyr Phe Pro Cys Thr Lys Ser Tyr
850                 855                 860

Trp Phe Gly Glu Glu Ser Asp Glu Lys Ser His Pro Gly Ser Asn Gln
865                 870                 875                 880

Lys Arg Ile Ser Glu Ile Cys Met Glu Glu Pro Thr His Leu Lys
                885                 890                 895

Leu Gly Val Ser Ile Gln Asn Leu Val Lys Val Tyr Arg Asp Gly Met
            900                 905                 910

Lys Val Ala Val Asp Gly Leu Ala Leu Asn Phe Tyr Glu Gly Gln Ile
            915                 920                 925

Thr Ser Phe Leu Gly His Asn Gly Ala Gly Lys Thr Thr Met Ser
930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Thr Ile Arg Gln Asn Leu Gly
                965                 970                 975

Val Cys Pro Gln His Asn Val Leu Phe Asp Met Leu Thr Val Glu Glu
                980                 985                 990

His Ile Trp Phe Tyr Ala Arg Leu Lys Gly Leu Ser Glu Lys His Val
            995                 1000                1005

Lys Ala Glu Met Glu Gln Met Ala Leu Asp Val Gly Leu Pro Ser
    1010                1015                1020

Ser Lys Leu Lys Ser Lys Thr Ser Gln Leu Ser Gly Gly Met Gln
    1025                1030                1035

Arg Lys Leu Ser Val Ala Leu Ala Phe Val Gly Gly Ser Lys Val
    1040                1045                1050

Val Ile Leu Asp Glu Pro Thr Ala Gly Val Asp Pro Tyr Ser Arg
    1055                1060                1065

Arg Gly Ile Trp Glu Leu Leu Leu Lys Tyr Arg Gln Gly Arg Thr
    1070                1075                1080

Ile Ile Leu Ser Thr His His Met Asp Glu Ala Asp Val Leu Gly
    1085                1090                1095
```

-continued

```
Asp Arg Ile Ala Ile Ile Ser His Gly Lys Leu Cys Cys Val Gly
    1100                1105                1110

Ser Ser Leu Phe Leu Lys Asn Gln Leu Gly Thr Gly Tyr Tyr Leu
    1115                1120                1125

Thr Leu Val Lys Lys Asp Val Glu Ser Ser Leu Ser Ser Cys Arg
    1130                1135                1140

Asn Ser Ser Ser Thr Val Ser Tyr Leu Lys Lys Glu Asp Ser Val
    1145                1150                1155

Ser Gln Ser Ser Ser Asp Ala Gly Leu Gly Ser Asp His Glu Ser
    1160                1165                1170

Asp Thr Leu Thr Ile Asp Val Ser Ala Ile Ser Asn Leu Ile Arg
    1175                1180                1185

Lys His Val Ser Glu Ala Arg Leu Val Glu Asp Ile Gly His Glu
    1190                1195                1200

Leu Thr Tyr Val Leu Pro Tyr Glu Ala Ala Lys Glu Gly Ala Phe
    1205                1210                1215

Val Glu Leu Phe His Glu Ile Asp Asp Arg Leu Ser Asp Leu Gly
    1220                1225                1230

Ile Ser Ser Tyr Gly Ile Ser Glu Thr Thr Leu Glu Glu Ile Phe
    1235                1240                1245

Leu Lys Val Ala Glu Glu Ser Gly Val Asp Ala Glu Thr Ser Asp
    1250                1255                1260

Gly Thr Leu Pro Ala Arg Arg Asn Arg Arg Ala Phe Gly Asp Lys
    1265                1270                1275

Gln Ser Cys Leu Arg Pro Phe Thr Glu Asp Asp Ala Ala Asp Pro
    1280                1285                1290

Asn Asp Ser Asp Ile Asp Pro Glu Ser Arg Glu Thr Asp Leu Leu
    1295                1300                1305

Ser Gly Met Asp Gly Lys Gly Ser Tyr Gln Val Lys Gly Trp Lys
    1310                1315                1320

Leu Thr Gln Gln Gln Phe Val Ala Leu Leu Trp Lys Arg Leu Leu
    1325                1330                1335

Ile Ala Arg Arg Ser Arg Lys Gly Phe Phe Ala Gln Ile Val Leu
    1340                1345                1350

Pro Ala Val Phe Val Cys Ile Ala Leu Val Phe Ser Leu Ile Val
    1355                1360                1365

Pro Pro Phe Gly Lys Tyr Pro Ser Leu Glu Leu Gln Pro Trp Met
    1370                1375                1380

Tyr Asn Glu Gln Tyr Thr Phe Val Ser Asn Asp Ala Pro Glu Asp
    1385                1390                1395

Thr Gly Thr Leu Glu Leu Leu Asn Ala Leu Thr Lys Asp Pro Gly
    1400                1405                1410

Phe Gly Thr Arg Cys Met Glu Gly Asn Pro Ile Pro Asp Thr Pro
    1415                1420                1425

Cys Gln Ala Gly Glu Glu Glu Trp Thr Thr Ala Pro Val Pro Gln
    1430                1435                1440

Thr Ile Met Asp Leu Phe Gln Asn Gly Asn Trp Thr Met Gln Asn
    1445                1450                1455

Pro Ser Pro Ala Cys Gln Cys Ser Ser Asp Lys Ile Lys Lys Met
    1460                1465                1470

Leu Pro Val Cys Pro Pro Gly Ala Gly Gly Leu Pro Pro Pro Gln
    1475                1480                1485

Arg Lys Gln Asn Thr Ala Asp Ile Leu Gln Asp Leu Thr Gly Arg
```

-continued

|   |   |   | 1490 |   |   |   | 1495 |   |   |   | 1500 |
|---|---|---|------|---|---|---|------|---|---|---|------|

Asn Ile Ser Asp Tyr Leu Val Lys Thr Tyr Val Gln Ile Ile Ala
    1505                1510                1515

Lys Ser Leu Lys Asn Lys Ile Trp Val Asn Glu Phe Arg Tyr Gly
    1520                1525                1530

Gly Phe Ser Leu Gly Val Ser Asn Thr Gln Ala Leu Pro Pro Ser
    1535                1540                1545

Gln Glu Val Asn Asp Ala Ile Lys Gln Met Lys Lys His Leu Lys
    1550                1555                1560

Leu Ala Lys Asp Ser Ser Ala Asp Arg Phe Leu Asn Ser Leu Gly
    1565                1570                1575

Arg Phe Met Thr Gly Leu Asp Thr Lys Asn Asn Val Lys Val Trp
    1580                1585                1590

Phe Asn Asn Lys Gly Trp His Ala Ile Ser Ser Phe Leu Asn Val
    1595                1600                1605

Ile Asn Asn Ala Ile Leu Arg Ala Asn Leu Gln Lys Gly Glu Asn
    1610                1615                1620

Pro Ser His Tyr Gly Ile Thr Ala Phe Asn His Pro Leu Asn Leu
    1625                1630                1635

Thr Lys Gln Gln Leu Ser Glu Val Ala Leu Met Thr Thr Ser Val
    1640                1645                1650

Asp Val Leu Val Ser Ile Cys Val Ile Phe Ala Met Ser Phe Val
    1655                1660                1665

Pro Ala Ser Phe Val Val Phe Leu Ile Gln Glu Arg Val Ser Lys
    1670                1675                1680

Ala Lys His Leu Gln Phe Ile Ser Gly Val Lys Pro Val Ile Tyr
    1685                1690                1695

Trp Leu Ser Asn Phe Val Trp Asp Met Cys Asn Tyr Val Val Pro
    1700                1705                1710

Ala Thr Leu Val Ile Ile Phe Ile Cys Phe Gln Gln Lys Ser
    1715                1720                1725

Tyr Val Ser Ser Thr Asn Leu Pro Val Leu Ala Leu Leu Leu Leu
    1730                1735                1740

Leu Tyr Gly Trp Ser Ile Thr Pro Leu Met Tyr Pro Ala Ser Phe
    1745                1750                1755

Val Phe Lys Ile Pro Ser Thr Ala Tyr Val Val Leu Thr Ser Val
    1760                1765                1770

Asn Leu Phe Ile Gly Ile Asn Gly Ser Val Ala Thr Phe Val Leu
    1775                1780                1785

Glu Leu Phe Thr Asp Asn Lys Leu Asn Asn Ile Asn Asp Ile Leu
    1790                1795                1800

Lys Ser Val Phe Leu Ile Phe Pro His Phe Cys Leu Gly Arg Gly
    1805                1810                1815

Leu Ile Asp Met Val Lys Asn Gln Ala Met Ala Asp Ala Leu Glu
    1820                1825                1830

Arg Phe Gly Glu Asn Arg Phe Val Ser Pro Leu Ser Trp Asp Leu
    1835                1840                1845

Val Gly Arg Asn Leu Phe Ala Met Ala Val Glu Gly Val Val Phe
    1850                1855                1860

Phe Leu Ile Thr Val Leu Ile Gln Tyr Arg Phe Phe Ile Arg Pro
    1865                1870                1875

Arg Pro Val Asn Ala Lys Leu Ser Pro Leu Asn Asp Glu Asp Glu
    1880                1885                1890

Asp Val Arg Arg Glu Arg Gln Arg Ile Leu Asp Gly Gly Gly Gln
1895                 1900                1905

Asn Asp Ile Leu Glu Ile Lys Glu Leu Thr Lys Ile Tyr Arg Arg
1910                1915                1920

Lys Arg Lys Pro Ala Val Asp Arg Ile Cys Val Gly Ile Pro Pro
1925                1930                1935

Gly Glu Cys Phe Gly Leu Leu Gly Val Asn Gly Ala Gly Lys Ser
1940                1945                1950

Ser Thr Phe Lys Met Leu Thr Gly Asp Thr Thr Val Thr Arg Gly
1955                1960                1965

Asp Ala Phe Leu Asn Lys Asn Ser Ile Leu Ser Asn Ile His Glu
1970                1975                1980

Val His Gln Asn Met Gly Tyr Cys Pro Gln Phe Asp Ala Ile Thr
1985                1990                1995

Glu Leu Leu Thr Gly Arg Glu His Val Glu Phe Phe Ala Leu Leu
2000                2005                2010

Arg Gly Val Pro Glu Lys Glu Val Gly Lys Val Gly Glu Trp Ala
2015                2020                2025

Ile Arg Lys Leu Gly Leu Val Lys Tyr Gly Glu Lys Tyr Ala Gly
2030                2035                2040

Asn Tyr Ser Gly Gly Asn Lys Arg Lys Leu Ser Thr Ala Met Ala
2045                2050                2055

Leu Ile Gly Gly Pro Pro Val Val Phe Leu Asp Glu Pro Thr Thr
2060                2065                2070

Gly Met Asp Pro Lys Ala Arg Arg Phe Leu Trp Asn Cys Ala Leu
2075                2080                2085

Ser Val Val Lys Glu Gly Arg Ser Val Val Leu Thr Ser His Ser
2090                2095                2100

Met Glu Glu Cys Glu Ala Leu Cys Thr Arg Met Ala Ile Met Val
2105                2110                2115

Asn Gly Arg Phe Arg Cys Leu Gly Ser Val Gln His Leu Lys Asn
2120                2125                2130

Arg Phe Gly Asp Gly Tyr Thr Ile Val Val Arg Ile Ala Gly Ser
2135                2140                2145

Asn Pro Asp Leu Lys Pro Val Gln Asp Phe Phe Gly Leu Ala Phe
2150                2155                2160

Pro Gly Ser Val Leu Lys Glu Lys His Arg Asn Met Leu Gln Tyr
2165                2170                2175

Gln Leu Pro Ser Ser Leu Ser Ser Leu Ala Arg Ile Phe Ser Ile
2180                2185                2190

Leu Ser Gln Ser Lys Lys Arg Leu His Ile Glu Asp Tyr Ser Val
2195                2200                2205

Ser Gln Thr Thr Leu Asp Gln Val Phe Val Asn Phe Ala Lys Asp
2210                2215                2220

Gln Ser Asp Asp Asp His Leu Lys Asp Leu Ser Leu His Lys Asn
2225                2230                2235

Gln Thr Val Val Asp Val Ala Val Leu Thr Ser Phe Leu Gln Asp
2240                2245                2250

Glu Lys Val Lys Glu Ser Tyr Val
2255                2260

<210> SEQ ID NO 8
<211> LENGTH: 780

```
<212> TYPE: DNA
<213> ORGANISM: Rattus norvegicus
<220> FEATURE:
<221> NAME/KEY: CDS
<222> LOCATION: (63)..(731)

<400> SEQUENCE: 8
gcagctttaa gtagagagtg gattttttgtc tcagtttgtc ttctgtttgc gactctgaaa      60 ga atg ctg tgg gca ctc ttt ttc ctg gtg act act att cac gct gaa         107
   Met Leu Trp Ala Leu Phe Phe Leu Val Thr Thr Ile His Ala Glu
   1               5                   10                  15 ctc tgc cgt cca gat gca gaa aat gcc ttt aaa gta aga ctt agc atc        155
Leu Cys Arg Pro Asp Ala Glu Asn Ala Phe Lys Val Arg Leu Ser Ile
                20                  25                  30 aaa gca gct ctt gga gat aaa gcg tat gtc tgg gac aca gat gaa gaa        203
Lys Ala Ala Leu Gly Asp Lys Ala Tyr Val Trp Asp Thr Asp Glu Glu
                35                  40                  45 tat ctc ttc aga gca atg gtg gca ttc tcc atg aga aaa gtt ccc aac        251
Tyr Leu Phe Arg Ala Met Val Ala Phe Ser Met Arg Lys Val Pro Asn
        50                  55                  60 aga gaa gga aca gaa att tcc cac gtc ctg ctt tgc aat gta acc cag        299
Arg Glu Gly Thr Glu Ile Ser His Val Leu Leu Cys Asn Val Thr Gln
65                  70                  75 aga gtg tca ttc tgg ttt gtg gtc aca gac cct ttg aaa aac cat act        347
Arg Val Ser Phe Trp Phe Val Val Thr Asp Pro Leu Lys Asn His Thr
80                  85                  90                  95 ctt cct gca gct gaa gta cag tca gcc ata aga atg aac agg aac cgg        395
Leu Pro Ala Ala Glu Val Gln Ser Ala Ile Arg Met Asn Arg Asn Arg
                100                 105                 110 atc aac agt gca ttc ttt ttg gat gat cat act ctg gaa ttt tta aaa        443
Ile Asn Ser Ala Phe Phe Leu Asp Asp His Thr Leu Glu Phe Leu Lys
                115                 120                 125 att cct tcc act ctt gct ccc ccg atg gat cca tct gtg ccc gtc tgg        491
Ile Pro Ser Thr Leu Ala Pro Pro Met Asp Pro Ser Val Pro Val Trp
            130                 135                 140 att att gta ttt ggt gtg ata ttt tgc att gtt aca gtt gca att gca        539
Ile Ile Val Phe Gly Val Ile Phe Cys Ile Val Thr Val Ala Ile Ala
            145                 150                 155 cta ctg gtt tta tcc gga atc cgg caa cga aga agg aac aag aaa gga        587
Leu Leu Val Leu Ser Gly Ile Arg Gln Arg Arg Arg Asn Lys Lys Gly
160                 165                 170                 175 cca cct gga gtg gag gat gca gaa gac aag tgt gaa aac atc atc aca        635
Pro Pro Gly Val Glu Asp Ala Glu Asp Lys Cys Glu Asn Ile Ile Thr
                180                 185                 190 att gaa aat ggc atc cct tgt gat ccc ttg gac atg aag gga ggg cac        683
Ile Glu Asn Gly Ile Pro Cys Asp Pro Leu Asp Met Lys Gly Gly His
                195                 200                 205 att aat gat ggc ttc ttg aca gag gat gag cgt ctc acc cct ctc tga        731
Ile Asn Asp Gly Phe Leu Thr Glu Asp Glu Arg Leu Thr Pro Leu
            210                 215                 220 gagttacagt cttgtaagaa aatttcaaga tgcttgaatg tgatagaca                   780

<210> SEQ ID NO 9
<211> LENGTH: 222
<212> TYPE: PRT
<213> ORGANISM: Rattus norvegicus

<400> SEQUENCE: 9

Met Leu Trp Ala Leu Phe Phe Leu Val Thr Thr Ile His Ala Glu Leu
1               5                   10                  15
```

-continued

```
Cys Arg Pro Asp Ala Glu Asn Ala Phe Lys Val Arg Leu Ser Ile Lys
             20                  25                  30
Ala Ala Leu Gly Asp Lys Ala Tyr Val Trp Asp Thr Asp Glu Glu Tyr
         35                  40                  45
Leu Phe Arg Ala Met Val Ala Phe Ser Met Arg Lys Val Pro Asn Arg
 50                  55                  60
Glu Gly Thr Glu Ile Ser His Val Leu Leu Cys Asn Val Thr Gln Arg
 65                  70                  75                  80
Val Ser Phe Trp Phe Val Val Thr Asp Pro Leu Lys Asn His Thr Leu
                 85                  90                  95
Pro Ala Ala Glu Val Gln Ser Ala Ile Arg Met Asn Arg Asn Arg Ile
            100                 105                 110
Asn Ser Ala Phe Phe Leu Asp Asp His Thr Leu Glu Phe Leu Lys Ile
        115                 120                 125
Pro Ser Thr Leu Ala Pro Pro Met Asp Pro Ser Val Pro Val Trp Ile
130                 135                 140
Ile Val Phe Gly Val Ile Phe Cys Ile Val Thr Val Ala Ile Ala Leu
145                 150                 155                 160
Leu Val Leu Ser Gly Ile Arg Gln Arg Arg Asn Lys Lys Gly Pro
                165                 170                 175
Pro Gly Val Glu Asp Ala Glu Asp Lys Cys Glu Asn Ile Ile Thr Ile
            180                 185                 190
Glu Asn Gly Ile Pro Cys Asp Pro Leu Asp Met Lys Gly Gly His Ile
        195                 200                 205
Asn Asp Gly Phe Leu Thr Glu Asp Glu Arg Leu Thr Pro Leu
210                 215                 220

<210> SEQ ID NO 10
<211> LENGTH: 1116
<212> TYPE: DNA
<213> ORGANISM: Plasmodium falciparum
<220> FEATURE:
<221> NAME/KEY: CDS
<222> LOCATION: (1)..(1116)

<400> SEQUENCE: 10 atg cat ata gtg agc ttt att att ttt ttc ttt gca tta ttt ttt cca      48
Met His Ile Val Ser Phe Ile Ile Phe Phe Phe Ala Leu Phe Phe Pro
1                5                  10                  15 att tcc atc tgt tat aaa ata aat ggg gta tgt gat ttt tcg agc gaa      96
Ile Ser Ile Cys Tyr Lys Ile Asn Gly Val Cys Asp Phe Ser Ser Glu
             20                  25                  30 ggg cta agt ttg ttg cca gaa gaa aag tta gat ttt tct gta tca agg     144
Gly Leu Ser Leu Leu Pro Glu Glu Lys Leu Asp Phe Ser Val Ser Arg
         35                  40                  45 aat gta gat aaa tta tct gat gaa aac aat gta aga cat tgt gta cat     192
Asn Val Asp Lys Leu Ser Asp Glu Asn Asn Val Arg His Cys Val His
 50                  55                  60 ttt agt aag ggt ttt gaa tat tta cgt ttt ata tgt cca atg aga aaa     240
Phe Ser Lys Gly Phe Glu Tyr Leu Arg Phe Ile Cys Pro Met Arg Lys
 65                  70                  75                  80 gat aat tat gaa gga att gaa att cgt cct gtt gaa tgt ttt gaa tat     288
Asp Asn Tyr Glu Gly Ile Glu Ile Arg Pro Val Glu Cys Phe Glu Tyr
                 85                  90                  95 att cat att gaa gga aga gaa cac aaa tta agc gag ata tta aaa ggt     336
Ile His Ile Glu Gly Arg Glu His Lys Leu Ser Glu Ile Leu Lys Gly
            100                 105                 110 agt tta tat gaa aaa agt ata aat gat aat ata atg acg aga gat gtt     384
Ser Leu Tyr Glu Lys Ser Ile Asn Asp Asn Ile Met Thr Arg Asp Val
```

```
Ser Leu Tyr Glu Lys Ser Ile Asn Asp Asn Ile Met Thr Arg Asp Val
        115                 120                 125 ttt att cct cca act att tat gaa gat atg ttt ttt gaa tgt aca tgt    432
Phe Ile Pro Pro Thr Ile Tyr Glu Asp Met Phe Phe Glu Cys Thr Cys
130                 135                 140 gat aat agt tta acc ttt aaa aat aat atg att ggt ata aga ggt ata    480
Asp Asn Ser Leu Thr Phe Lys Asn Asn Met Ile Gly Ile Arg Gly Ile
145                 150                 155                 160 atg aaa atc cat tta aaa aaa aat att tta tat gga tgt gat ttt gat    528
Met Lys Ile His Leu Lys Lys Asn Ile Leu Tyr Gly Cys Asp Phe Asp
        165                 170                 175 cat gat gaa aaa tta atg aaa aat aaa aca gca ttt aca aat ttt tat    576
His Asp Glu Lys Leu Met Lys Asn Lys Thr Ala Phe Thr Asn Phe Tyr
        180                 185                 190 gat aaa caa aaa att tta cca tta ata ggt aat aat aat aat gat gat    624
Asp Lys Gln Lys Ile Leu Pro Leu Ile Gly Asn Asn Asn Asn Asp Asp
        195                 200                 205 gat aat aat gat gat gat aat aat aat gat aat aat aat aat gat aat    672
Asp Asn Asn Asp Asp Asp Asn Asn Asn Asp Asn Asn Asn Asn Asp Asn
210                 215                 220 aat aat aat aat aat aat aat aat aat aat aat aat aat aat aat aat    720
Asn Asn Asn Asn Asn Asn Asn Asn Asn Asn Asn Asn Asn Asn Asn Asn
225                 230                 235                 240 aat aat att act tgt aat gtt act att aaa aaa tct caa gtt tat tta    768
Asn Asn Ile Thr Cys Asn Val Thr Ile Lys Lys Ser Gln Val Tyr Leu
                245                 250                 255 gga att ata tgc cca gat gga tat act tta tat cca aat gat tgt ttt    816
Gly Ile Ile Cys Pro Asp Gly Tyr Thr Leu Tyr Pro Asn Asp Cys Phe
            260                 265                 270 aaa aat gtt ata tat gat aat aat att att ata cca tta aaa aaa att    864
Lys Asn Val Ile Tyr Asp Asn Asn Ile Ile Ile Pro Leu Lys Lys Ile
        275                 280                 285 ata cca cat gat att tta tat cat caa gac aaa aac aaa aga att act    912
Ile Pro His Asp Ile Leu Tyr His Gln Asp Lys Asn Lys Arg Ile Thr
290                 295                 300 ttt gct tca ttt aca tta aat ata aat gaa aat cca cca gga ttc aca    960
Phe Ala Ser Phe Thr Leu Asn Ile Asn Glu Asn Pro Pro Gly Phe Thr
305                 310                 315                 320 tgt tat tgt att aaa gat caa aca aat att aat aac cca ctt atc gta    1008
Cys Tyr Cys Ile Lys Asp Gln Thr Asn Ile Asn Asn Pro Leu Ile Val
                325                 330                 335 aac ttc cat ttt tca aat caa gaa aca tca tat gca aca aaa aat aaa    1056
Asn Phe His Phe Ser Asn Gln Glu Thr Ser Tyr Ala Thr Lys Asn Lys
            340                 345                 350 aat ctc ttc ttt tat ttt att ttc atc ttc cct ttt ctt tat gtt att    1104
Asn Leu Phe Phe Tyr Phe Ile Phe Ile Phe Pro Phe Leu Tyr Val Ile
        355                 360                 365 ttg tta tta taa                                                    1116
Leu Leu Leu
        370

<210> SEQ ID NO 11
<211> LENGTH: 371
<212> TYPE: PRT
<213> ORGANISM: Plasmodium falciparum

<400> SEQUENCE: 11

Met His Ile Val Ser Phe Ile Ile Phe Phe Phe Ala Leu Phe Phe Pro
1               5                   10                  15

Ile Ser Ile Cys Tyr Lys Ile Asn Gly Val Cys Asp Phe Ser Ser Glu
```

```
            20                  25                  30
Gly Leu Ser Leu Leu Pro Glu Glu Lys Leu Asp Phe Ser Val Ser Arg
         35                  40                  45

Asn Val Asp Lys Leu Ser Asp Glu Asn Asn Val Arg His Cys Val His
 50                  55                  60

Phe Ser Lys Gly Phe Glu Tyr Leu Arg Phe Ile Cys Pro Met Arg Lys
 65                  70                  75                  80

Asp Asn Tyr Glu Gly Ile Glu Ile Arg Pro Val Glu Cys Phe Glu Tyr
                 85                  90                  95

Ile His Ile Glu Gly Arg Glu His Lys Leu Ser Glu Ile Leu Lys Gly
            100                 105                 110

Ser Leu Tyr Glu Lys Ser Ile Asn Asp Asn Ile Met Thr Arg Asp Val
        115                 120                 125

Phe Ile Pro Pro Thr Ile Tyr Glu Asp Met Phe Glu Cys Thr Cys
130                 135                 140

Asp Asn Ser Leu Thr Phe Lys Asn Asn Met Ile Gly Ile Arg Gly Ile
145                 150                 155                 160

Met Lys Ile His Leu Lys Lys Asn Ile Leu Tyr Gly Cys Asp Phe Asp
                165                 170                 175

His Asp Glu Lys Leu Met Lys Asn Lys Thr Ala Phe Thr Asn Phe Tyr
            180                 185                 190

Asp Lys Gln Lys Ile Leu Pro Leu Ile Gly Asn Asn Asn Asn Asp Asp
        195                 200                 205

Asp Asn Asn Asp Asp Asp Asn Asn Asp Asn Asn Asn Asn Asp Asn
210                 215                 220

Asn Asn Asn Asn Asn Asn Asn Asn Asn Asn Asn Asn Asn Asn Asn Asn
225                 230                 235                 240

Asn Asn Ile Thr Cys Asn Val Thr Ile Lys Lys Ser Gln Val Tyr Leu
                245                 250                 255

Gly Ile Ile Cys Pro Asp Gly Tyr Thr Leu Tyr Pro Asn Asp Cys Phe
            260                 265                 270

Lys Asn Val Ile Tyr Asp Asn Asn Ile Ile Pro Leu Lys Lys Ile
        275                 280                 285

Ile Pro His Asp Ile Leu Tyr His Gln Asp Lys Asn Lys Arg Ile Thr
290                 295                 300

Phe Ala Ser Phe Thr Leu Asn Ile Asn Glu Asn Pro Pro Gly Phe Thr
305                 310                 315                 320

Cys Tyr Cys Ile Lys Asp Gln Thr Asn Ile Asn Asn Pro Leu Ile Val
                325                 330                 335

Asn Phe His Phe Ser Asn Gln Glu Thr Ser Tyr Ala Thr Lys Asn Lys
            340                 345                 350

Asn Leu Phe Phe Tyr Phe Ile Phe Ile Phe Pro Phe Leu Tyr Val Ile
        355                 360                 365

Leu Leu Leu
    370

<210> SEQ ID NO 12
<211> LENGTH: 73
<212> TYPE: PRT
<213> ORGANISM: Cricetulus migratorius

<400> SEQUENCE: 12

Gln Arg Val Asp His His Phe Asn Glu Pro Val Thr Ile Ala Ile Ile
 1               5                  10                  15
```

```
Leu Gly Met Ile Ala Gly Ile Val Gly Thr Ile Leu Leu Ile Tyr Tyr
            20                  25                  30

Leu Ile Ser Leu Ile Thr Lys Lys Ile Ser Ala Asp Lys Gln Pro Pro
        35                  40                  45

Lys Ser Glu Asn Thr Asp Glu Pro Pro Ser Pro Ile Glu Gln Ile Ile
    50                  55                  60

Val Gln Glu Glu His Asp Ser Ile Val
65                  70
```

<210> SEQ ID NO 13
<211> LENGTH: 405
<212> TYPE: DNA
<213> ORGANISM: Artificial Sequence
<220> FEATURE:
<223> OTHER INFORMATION: Expression vector

<400> SEQUENCE: 13

| | | |
|---|---|---|
| gccgccacta tgaagttcct ggtgaatgtg gccttggtgt tcatggtggt gtacatcagc | 60 |
| ttcatctacg ctagccttaa gggtaccgag ctcggatcca ctagtgaatt cgatatctct | 120 |
| agagcggccg ctgactacaa agacgatgac gacaagcttt caccaattca acacgatttt | 180 |
| cctgcactag tgatgatact cataattttg ggcgtgatgg cagggattat cggaactatc | 240 |
| cttcttatct cttactgtat cagccgaatg acaaagaaaa gttcagttga catccaatct | 300 |
| cctgagggtg tgacaacag tgtgcctttg agttctattg agcagactcc taatgaagag | 360 |
| tcctccaatg ttagcggcgg ccatcaccat caccatcact gataa | 405 |

<210> SEQ ID NO 14
<211> LENGTH: 411
<212> TYPE: DNA
<213> ORGANISM: Artificial Sequence
<220> FEATURE:
<223> OTHER INFORMATION: Expression vector

<400> SEQUENCE: 14

| | | |
|---|---|---|
| gccgccacta tgaagttcct ggtgaatgtg gccttggtgt tcatggtggt gtacatcagc | 60 |
| ttcatctacg ctagccttaa gggtaccgag ctcggatcca ctagtgaatt cgatatctct | 120 |
| agagcggccg ctgactacaa agacgatgac gacaagcttc aaagagttga tcaccatttt | 180 |
| aatgagccag tgactatagc cattattttg ggcatgatcg ctggtatcgt tggaactatc | 240 |
| cttctcattt attacttaat cagcctaata acaagaaaa tttcagctga caaacaacct | 300 |
| cccaagagtg aaaacacgga tgagccacca agtcctattg aacagattat tgttcaagaa | 360 |
| gagcatgaca gcattgttag cggcggccat caccatcacc atcactgata a | 411 |

<210> SEQ ID NO 15
<211> LENGTH: 405
<212> TYPE: DNA
<213> ORGANISM: Artificial Sequence
<220> FEATURE:
<223> OTHER INFORMATION: Expression vector

<400> SEQUENCE: 15

| | | |
|---|---|---|
| gccgccacta tgaagttcct ggtgaatgtg gccttggtgt tcatggtggt gtacatcagc | 60 |
| ttcatctacg ctagccttaa gggtaccgag ctcggatcca ctagtgaatt cgatatcgac | 120 |
| gtcgcggccg ctgactacaa agacgatgac gacaagagcc taggccgc acacgatttt | 180 |
| cctgcactag tgatgatact cataattttg ggcgtgatgg cagggattat cggaactatc | 240 |
| cttcttatct cttactgtat cagccgaatg acaaagaaaa gttcagttga catccaatct | 300 |

```
cctgagggtg gtgacaacag tgtgcctttg agttctattg agcagactcc taatgaagag    360
tcctccaatg ttagcggcgg ccatcaccat caccatcact gataa                    405
```